(12) United States Patent
Itskovich et al.

(10) Patent No.: US 8,139,679 B2
(45) Date of Patent: *Mar. 20, 2012

(54) SYSTEM AND METHOD FOR CONTROLLING MODULATION

(75) Inventors: Mikhail Itskovich, Columbia, MD (US); Daniel S. Cohen, Baltimore, MD (US)

(73) Assignee: Atmel Corporation, San Jose, CA (US)

( * ) Notice: Subject to any disclaimer, the term of this patent is extended or adjusted under 35 U.S.C. 154(b) by 376 days.

This patent is subject to a terminal disclaimer.

(21) Appl. No.: 12/288,573

(22) Filed: Oct. 21, 2008

(65) Prior Publication Data

US 2009/0122913 A1    May 14, 2009

Related U.S. Application Data

(63) Continuation of application No. 10/972,990, filed on Oct. 25, 2004, now Pat. No. 7,440,515.

(51) Int. Cl.
*H03C 1/52* (2006.01)
*H04L 27/12* (2006.01)

(52) U.S. Cl. ......... 375/302; 375/282; 375/278; 375/322

(58) Field of Classification Search .................. 375/260, 375/261, 282, 130
See application file for complete search history.

(56) References Cited

U.S. PATENT DOCUMENTS

| | | | |
|---|---|---|---|
| 4,167,760 A * | 9/1979 | Decker | 360/40 |
| 4,706,261 A | 11/1987 | Torre et al. | |
| 4,808,937 A | 2/1989 | Correa et al. | |
| 5,050,189 A | 9/1991 | Cox et al. | |
| 5,469,468 A | 11/1995 | Schilling | |
| 5,822,362 A | 10/1998 | Friedmann | |
| 6,437,713 B1 | 8/2002 | Lesea | |
| 6,449,315 B2 * | 9/2002 | Richards | 375/282 |
| 6,486,990 B1 | 11/2002 | Roberts et al. | |
| 6,904,539 B2 | 6/2005 | Ueno | |
| 6,941,078 B1 * | 9/2005 | Onaka | 398/155 |
| 6,996,632 B2 | 2/2006 | Levy et al. | |
| 7,035,253 B2 | 4/2006 | Kuhlmann et al. | |
| 7,050,518 B1 | 5/2006 | Keller et al. | |
| 2001/0028686 A1 | 10/2001 | Richards | |
| 2002/0093909 A1 | 7/2002 | Wakabayashi | |
| 2003/0195645 A1 | 10/2003 | Pillay et al. | |

(Continued)

FOREIGN PATENT DOCUMENTS

| | | |
|---|---|---|
| WO | WO-2006047750 A2 | 5/2006 |
| WO | WO-2006047750 A3 | 5/2006 |

OTHER PUBLICATIONS

"International Application Serial No. PCT/US2005/38996, Search Report mailed Apr. 4, 2006", Downloaded from WIPO on Dec. 14, 2009.

(Continued)

*Primary Examiner* — Khanh C Tran
*Assistant Examiner* — Qutbuddin Ghulamali
(74) *Attorney, Agent, or Firm* — Fish & Richardson P.C.

(57) ABSTRACT

A system and method for controlling modulation. The system includes a plurality of modulators and a transmitting unit. The plurality of modulators decodes data from a data signal and also encodes the data into a clock signal. The transmitting unit transmits the encoded clock signal. According to the system and method disclosed herein, the present invention provides optimized coding efficiency while minimizing overall power consumption.

16 Claims, 53 Drawing Sheets

U.S. PATENT DOCUMENTS

2004/0066736 A1     4/2004    Kroeger
2004/0232997 A1   11/2004   Hein et al.
2005/0078712 A1     4/2005    Voutilainen
2006/0089151 A1     4/2006    Itskovich et al.

OTHER PUBLICATIONS

"International Application Serial No. PCT/US2005/38996, Written Opinion mailed Apr. 6, 2006".

"Taiwanese Application Serial No. 094137248, Non-Final Office Action dated Apr. 2, 2008", 5 pgs.

"Taiwanese Application Serial No. 094137248, Office Action mailed Mar. 30, 2009", 7 pgs.

Taiwanese Application Serial No. 094137248, Response filed Oct. 16, 2008 to Non-Final Office Action dated Apr. 2, 2008, 6 pgs.

\* cited by examiner

|  |  |  |  |
|---|---|---|---|
| FIG.1/1 | FIG.1/2 | FIG.1/3 | FIG.1/4 |
| FIG.1/5 | FIG.1/6 | FIG.1/7 | FIG.1/8 |
| FIG.1/9 | FIG.1/10 | FIG.1/11 | FIG.1/12 |
| FIG.1/13 | FIG.1/14 | FIG.1/15 | FIG.1/16 |

FIG.1  100

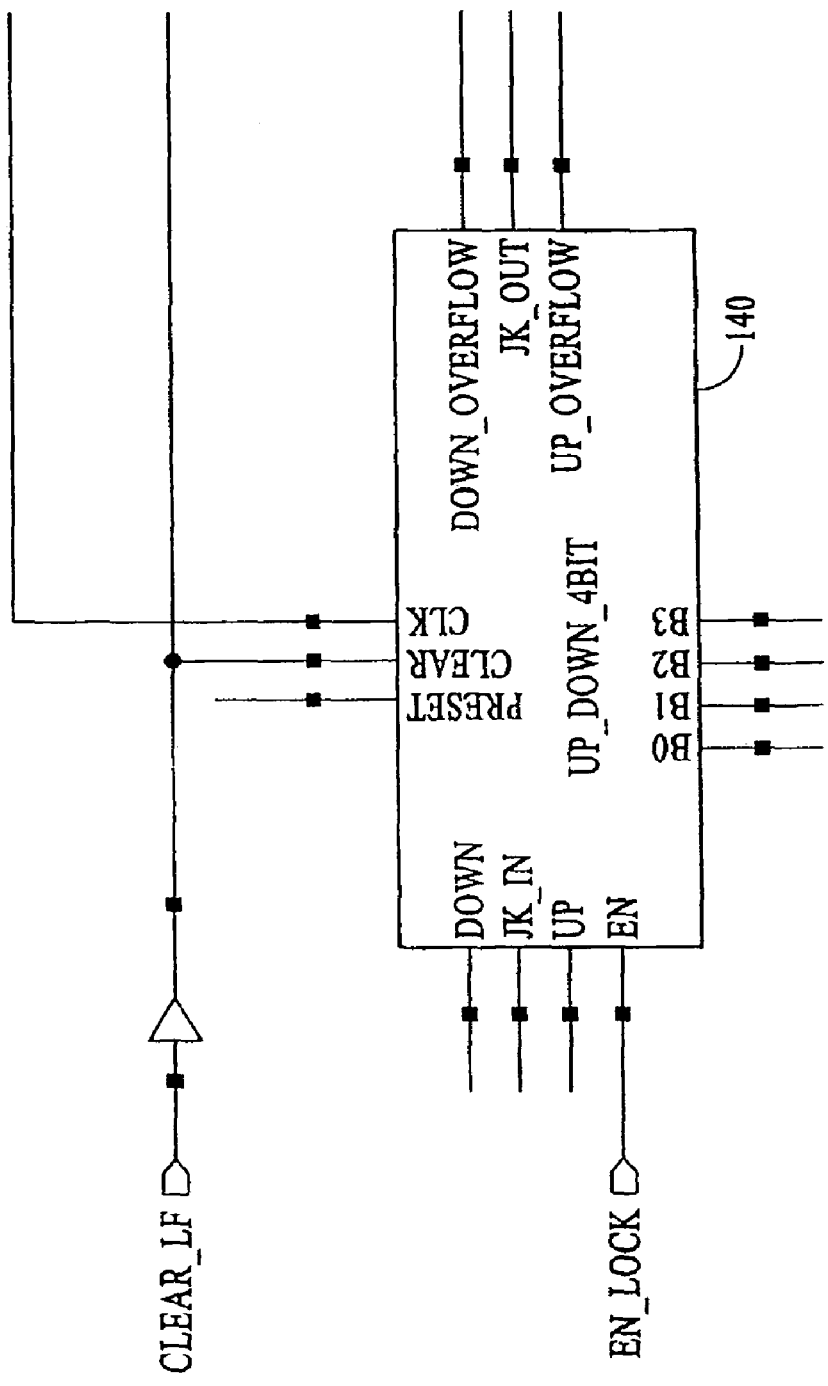
FIG.1/1

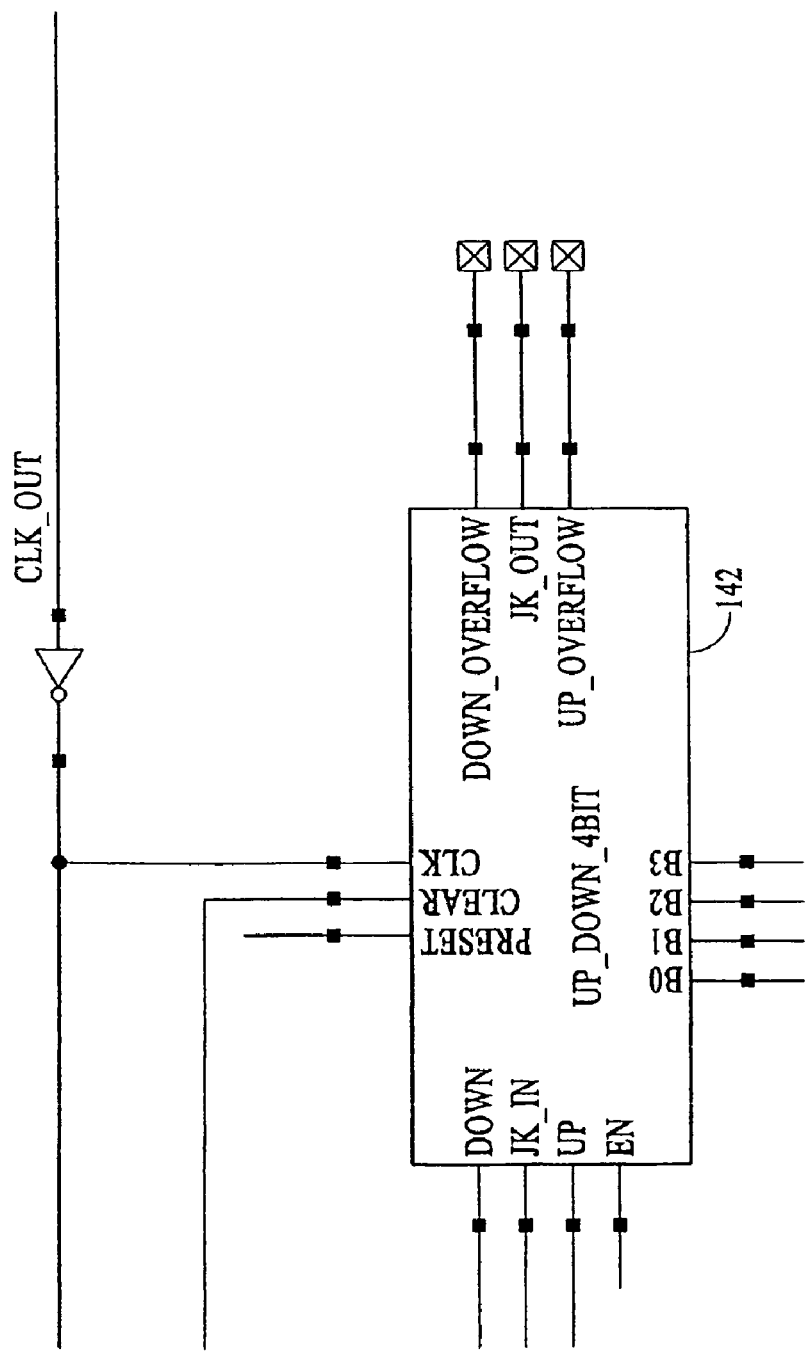
FIG.1/2

FIG.1/3

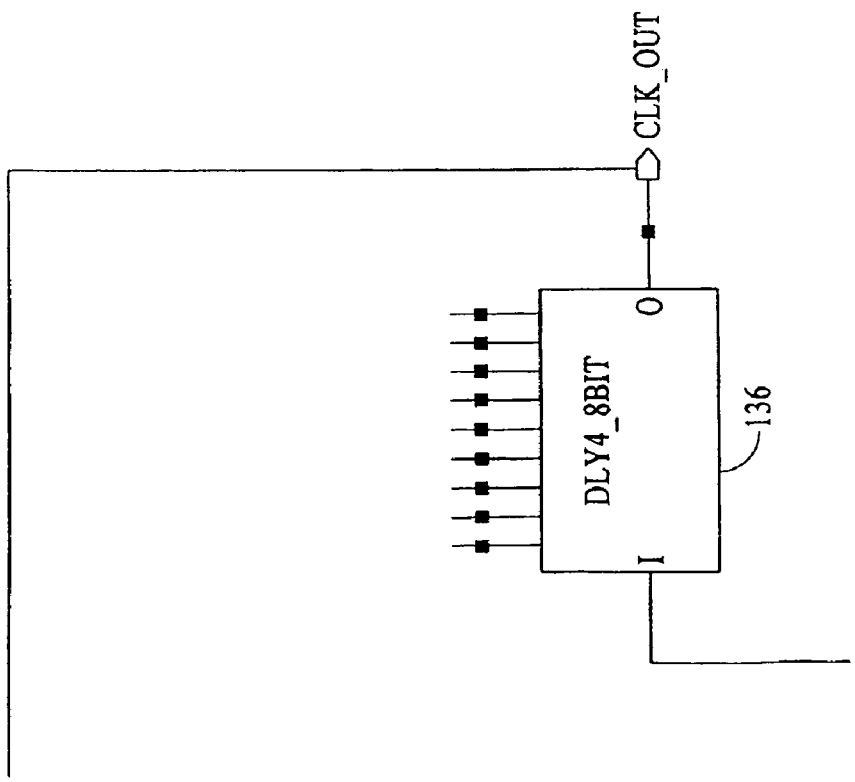

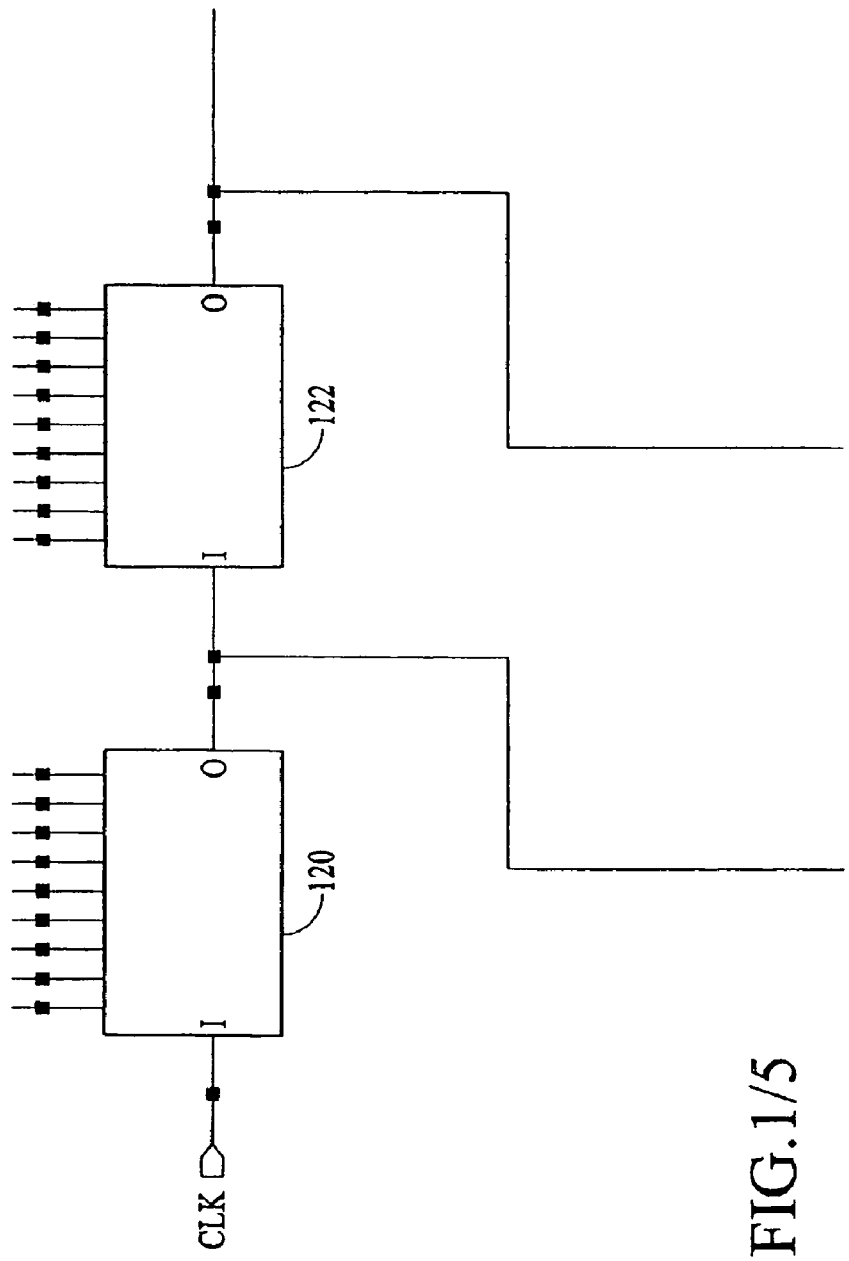
FIG.1/5

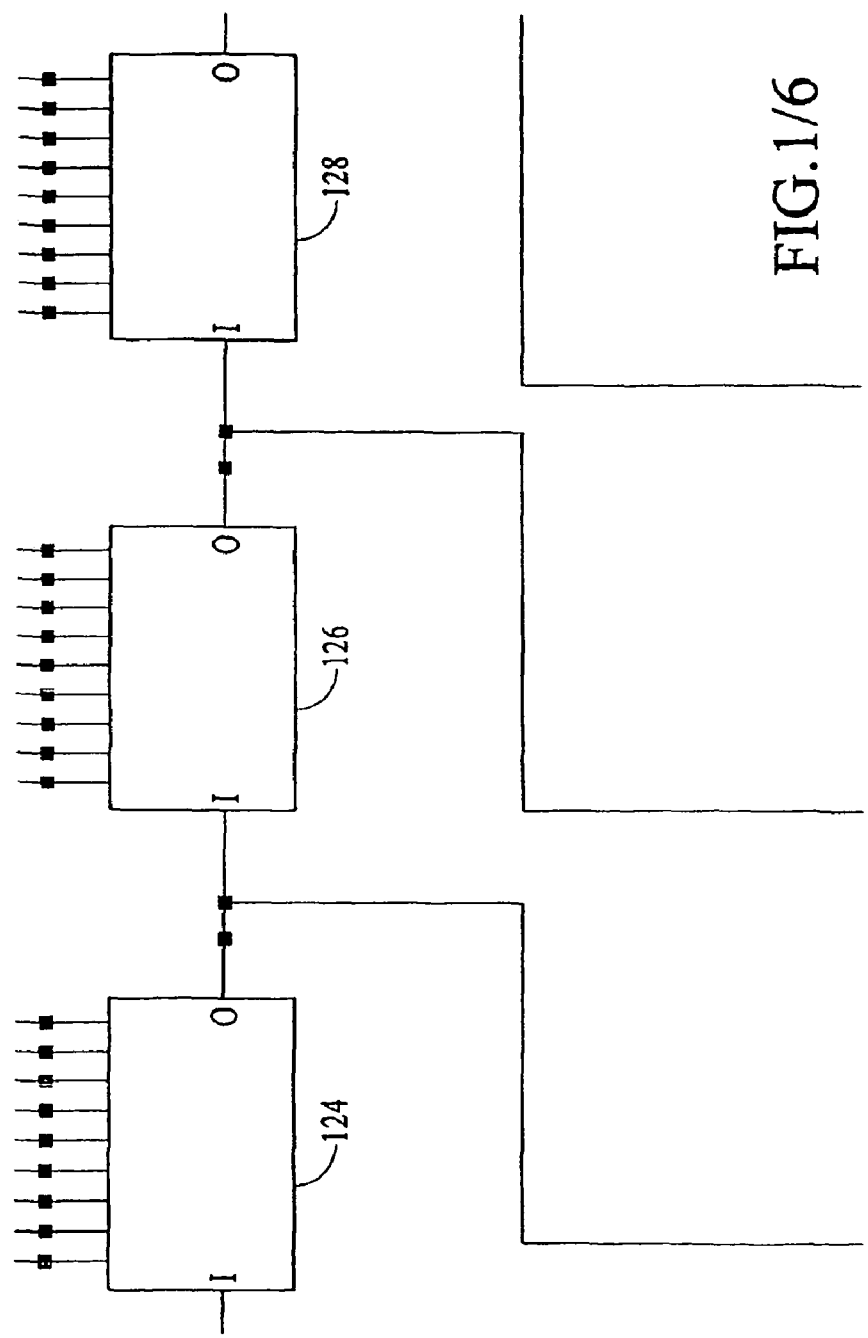
FIG.1/6

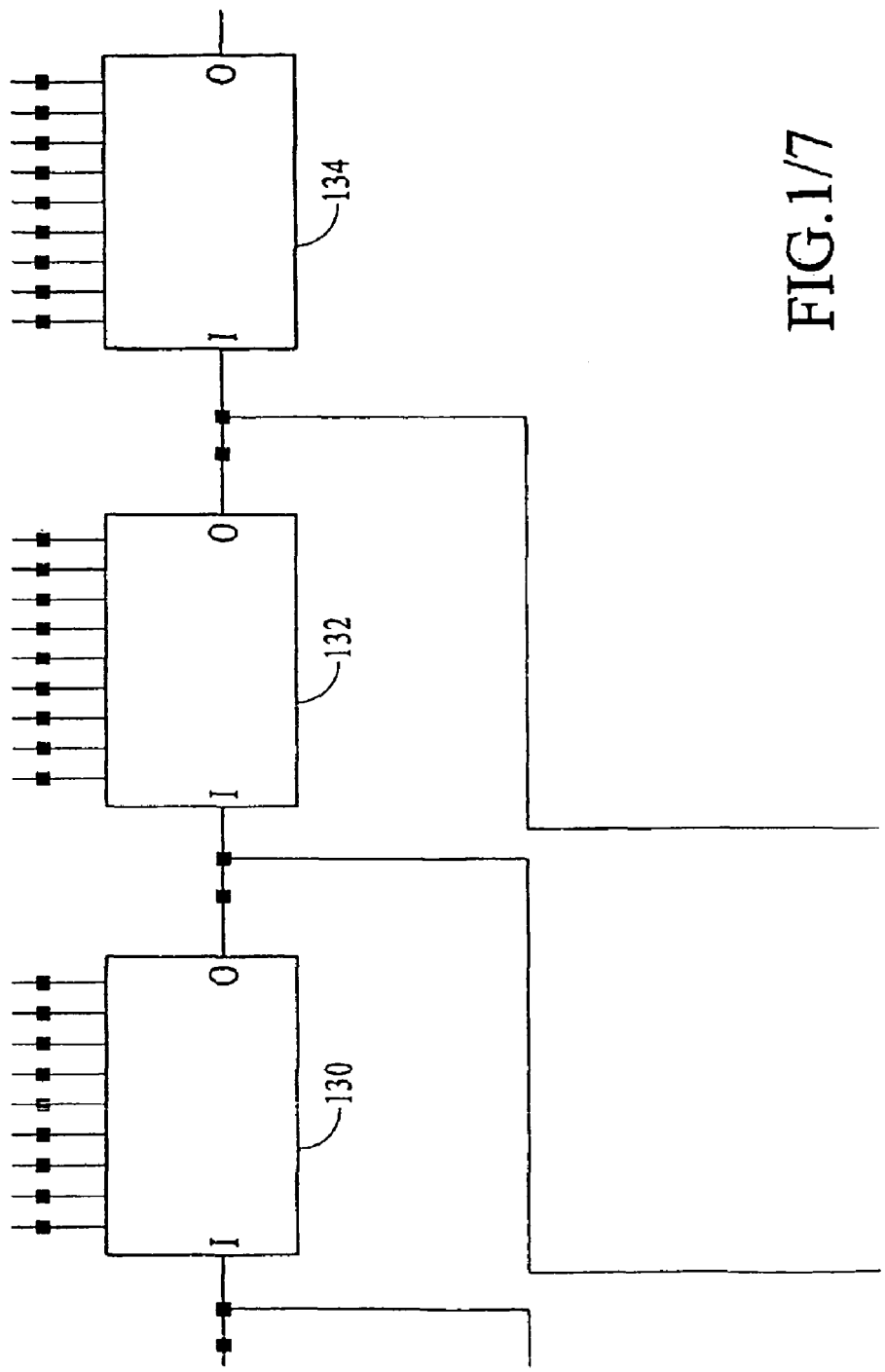

FIG.1/8

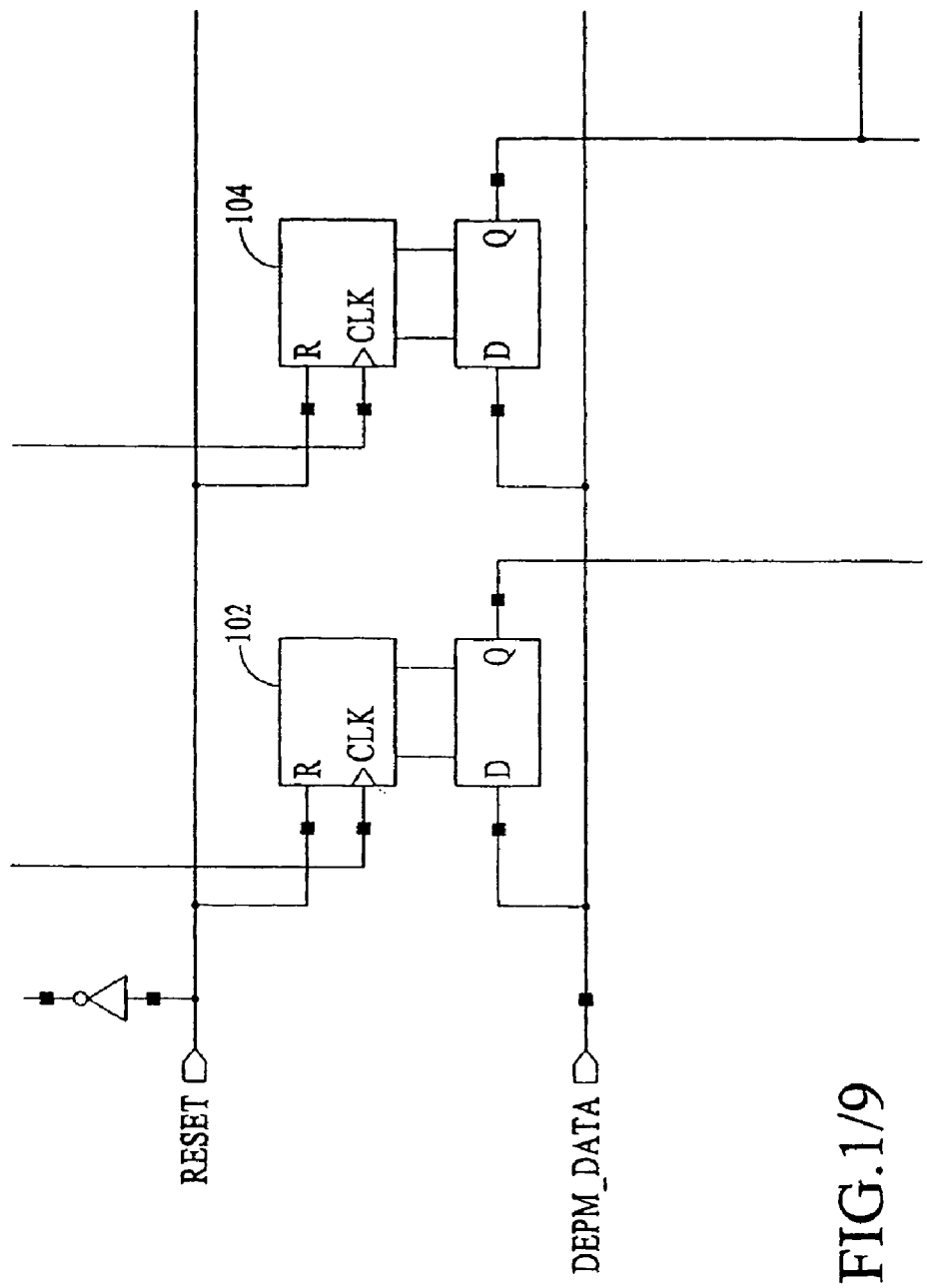
FIG.1/9

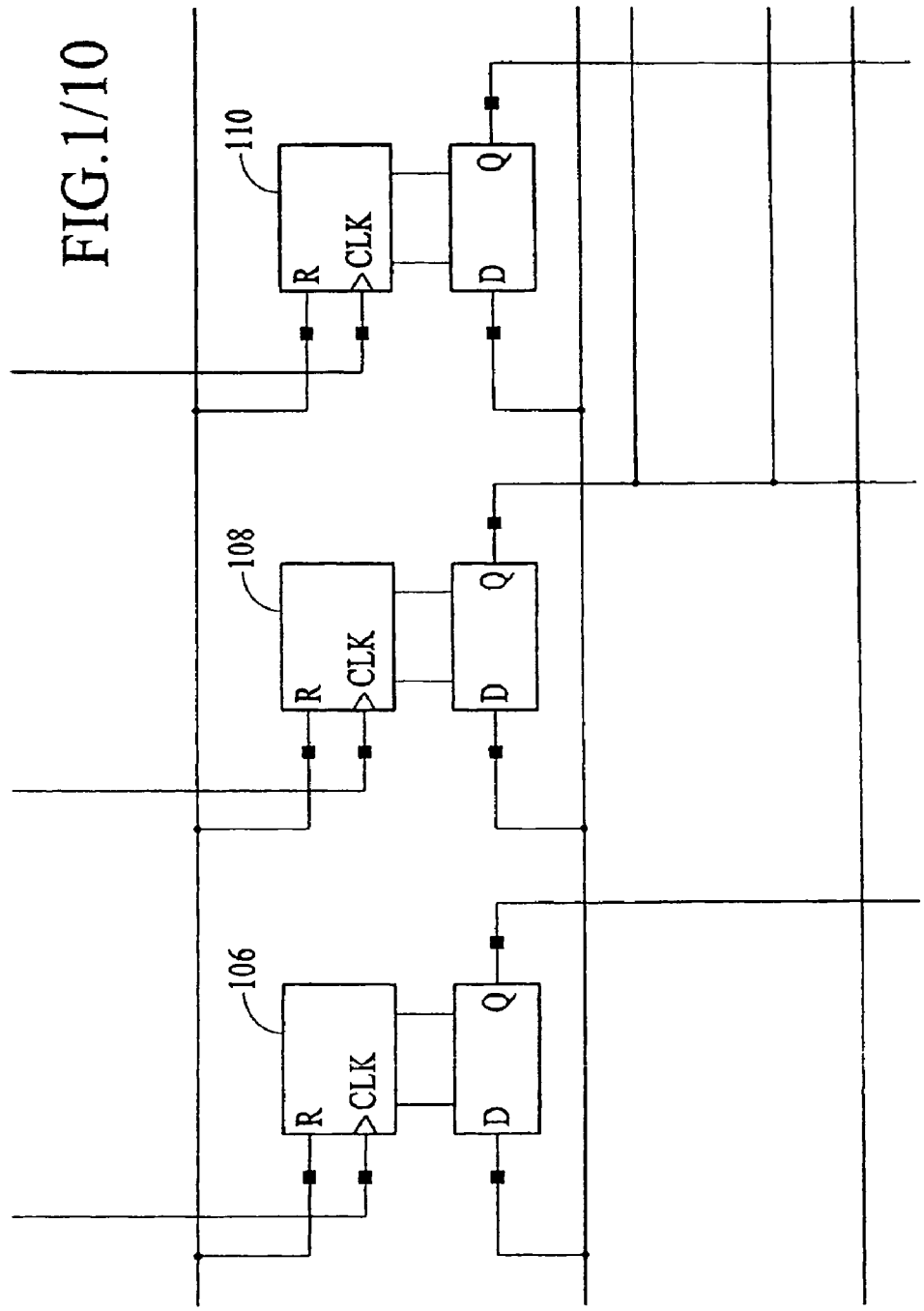

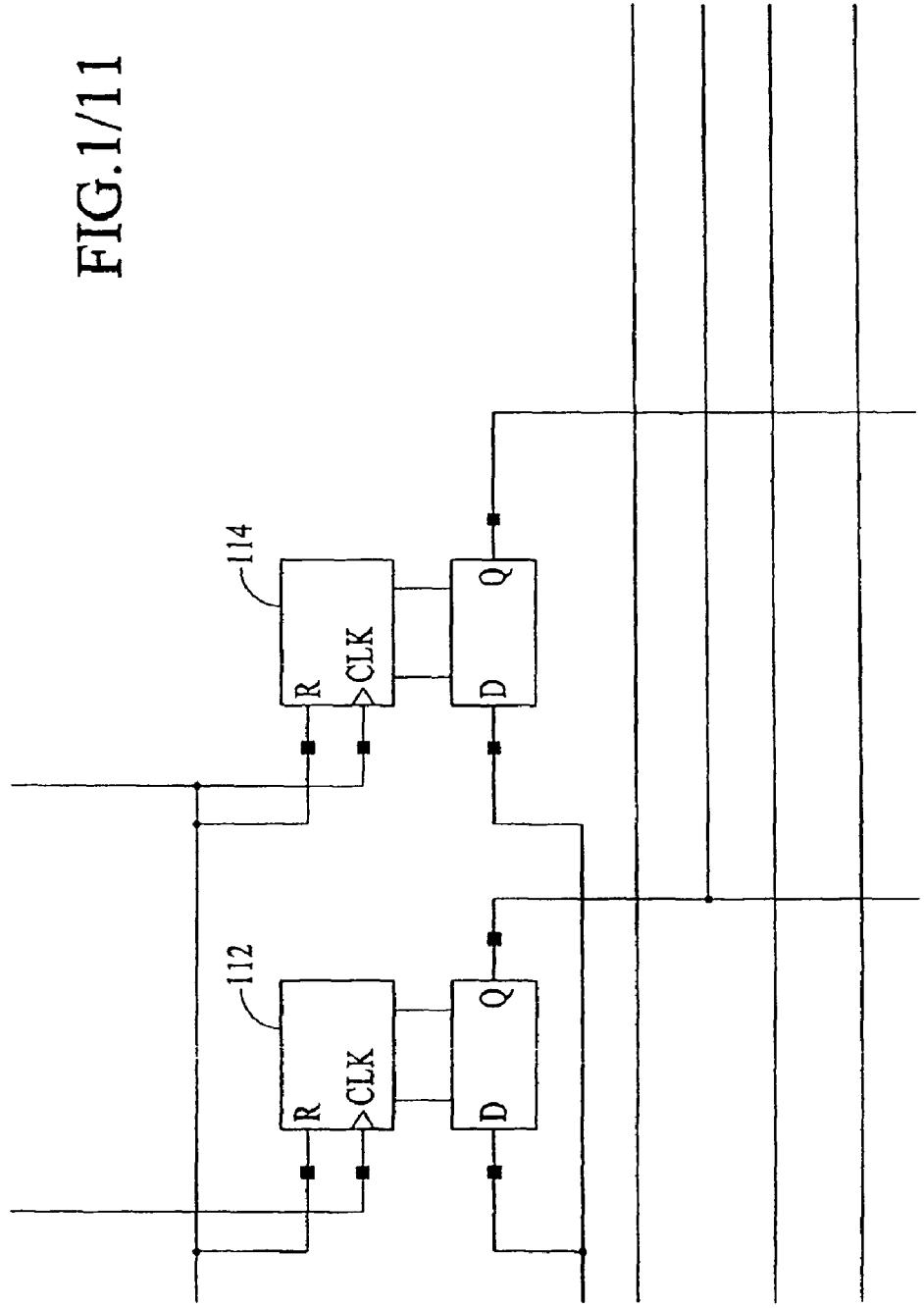
FIG.1/11

FIG.1/12
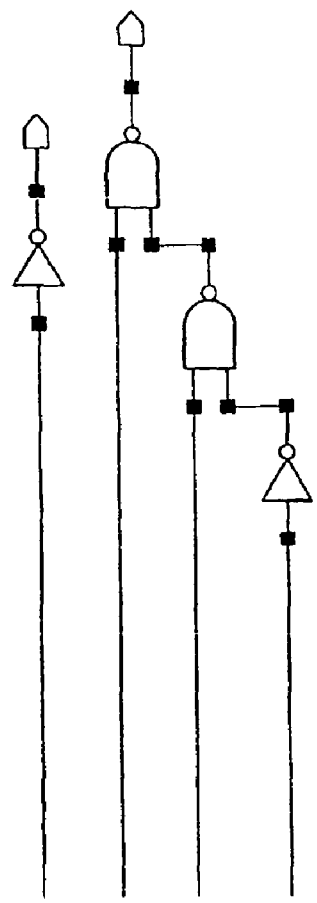

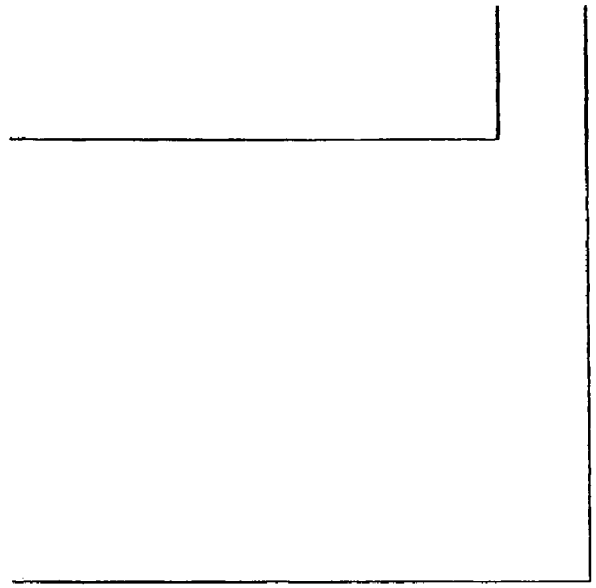
FIG.1/13

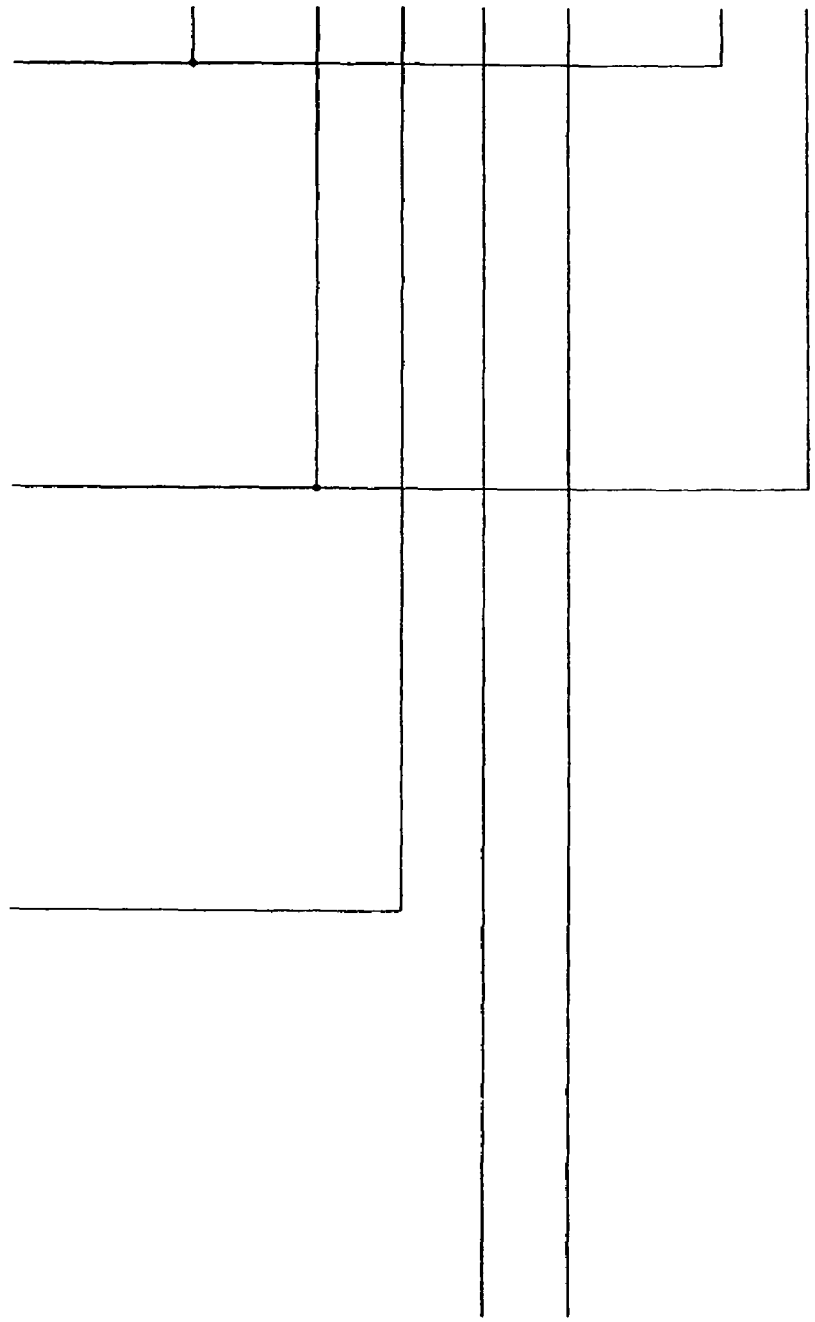
FIG.1/14

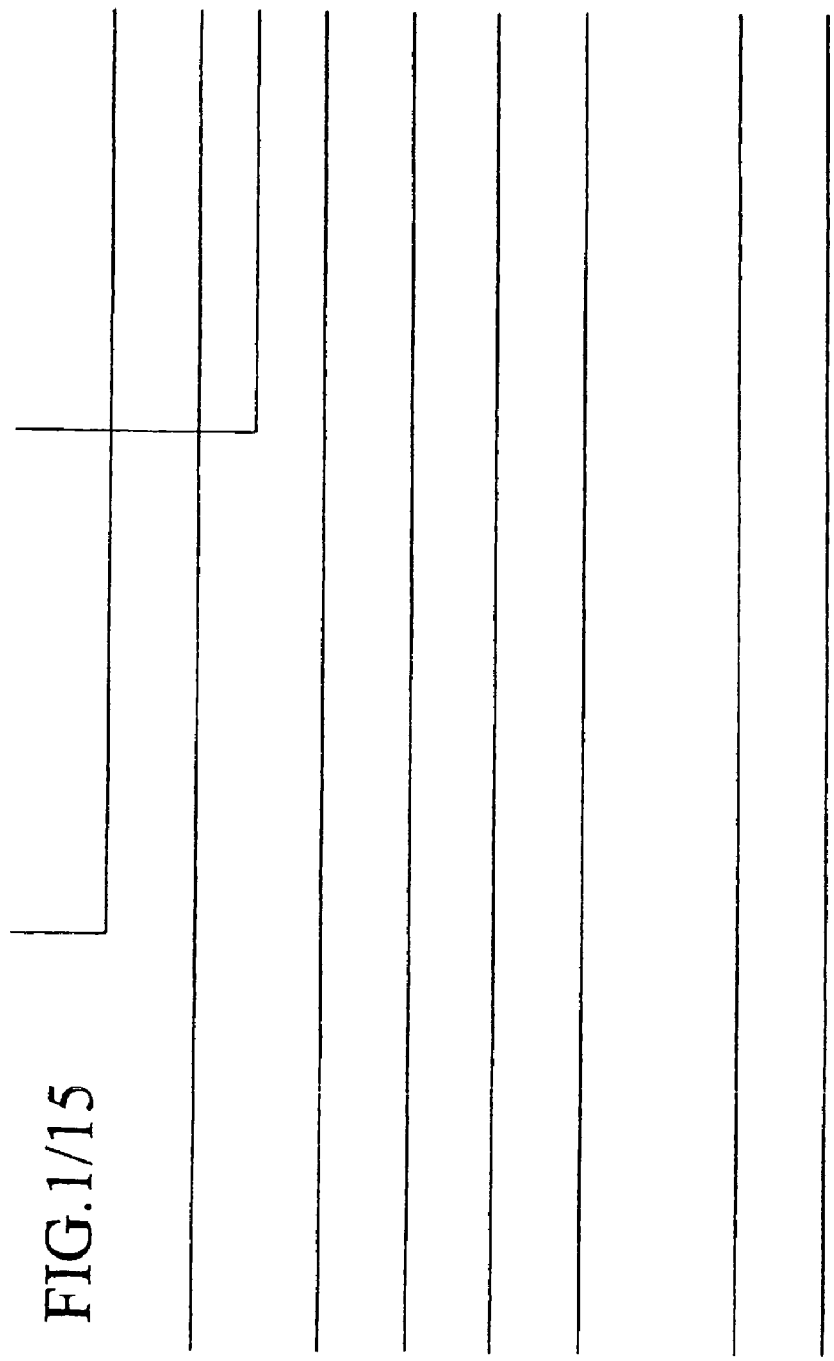

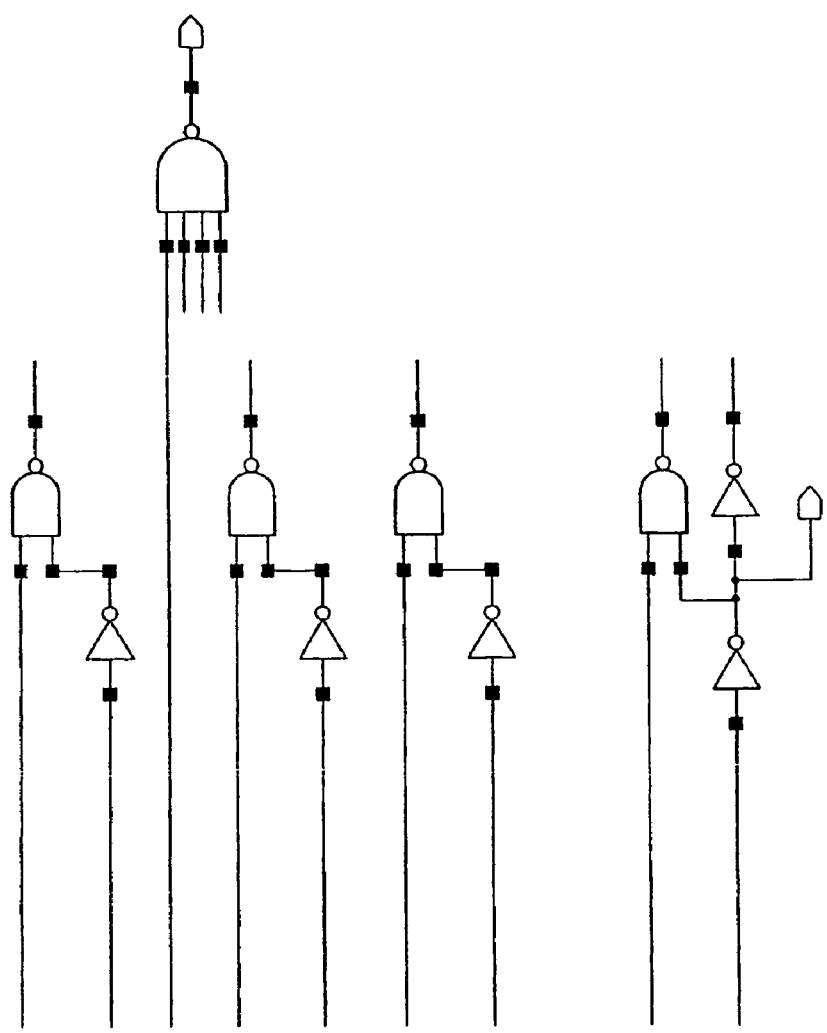
FIG.1/16

| FIG.3/1 | FIG.3/2 | FIG.3/3 | FIG.3/4 | FIG.3/5 | FIG.3/6 | FIG.3/7 |
|---------|---------|---------|---------|---------|---------|---------|
| FIG.3/8 | FIG.3/9 | FIG.3/10 | FIG.3/11 | FIG.3/12 | FIG.3/13 | FIG.3/14 |
| FIG.3/15 | | | | | FIG.3/16 | FIG.3/17 |

FIG.3

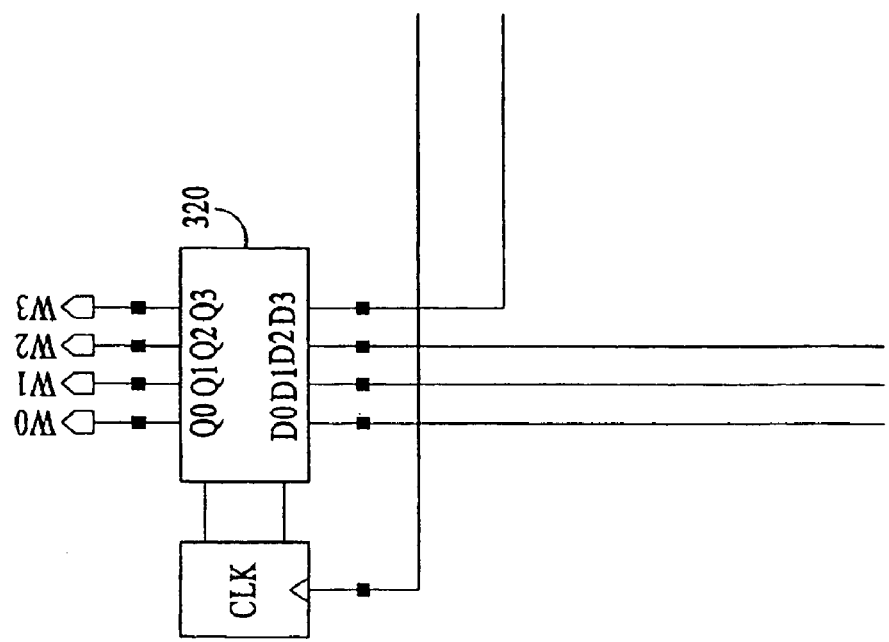
FIG.3/1

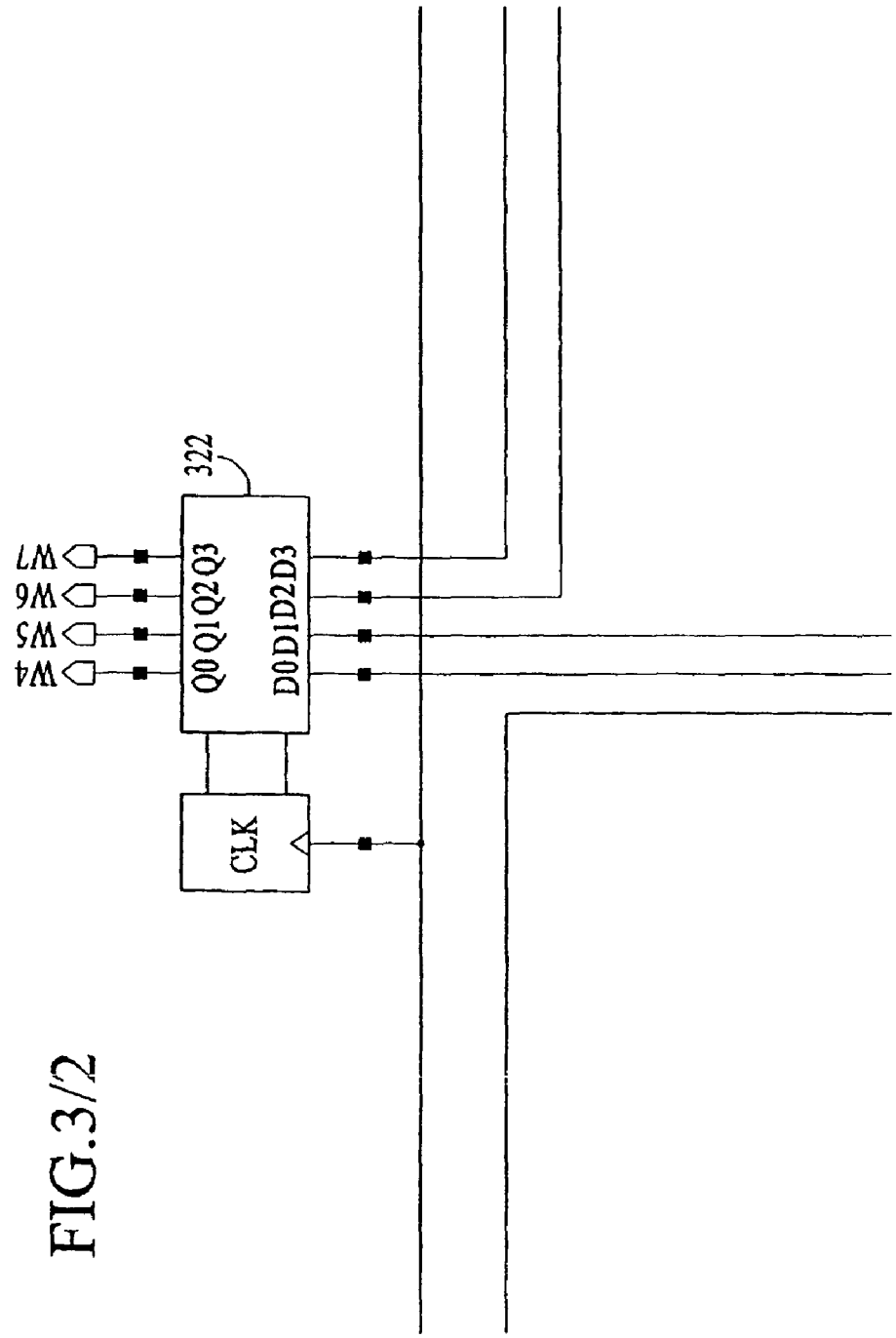
FIG.3/2

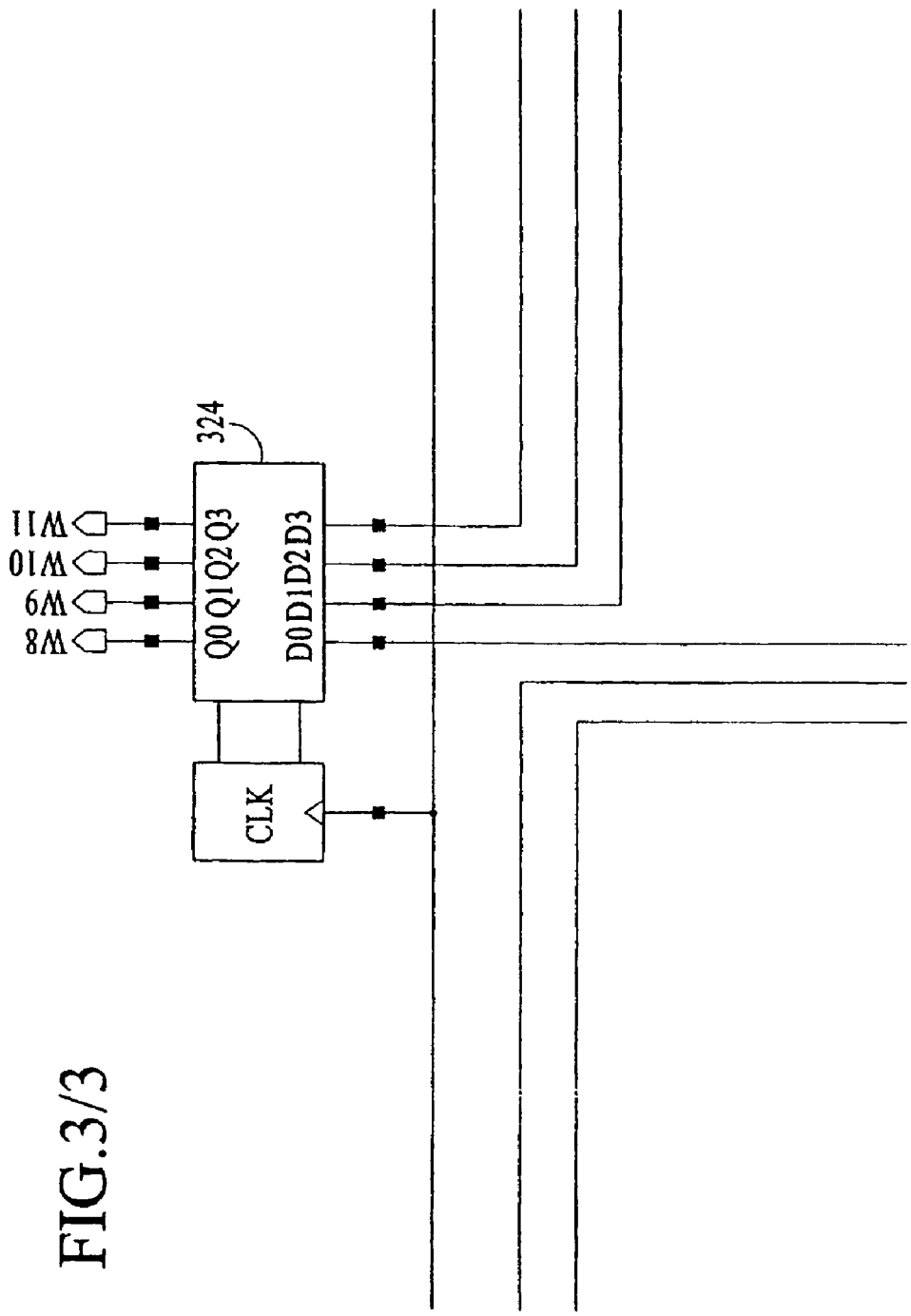
FIG.3/3

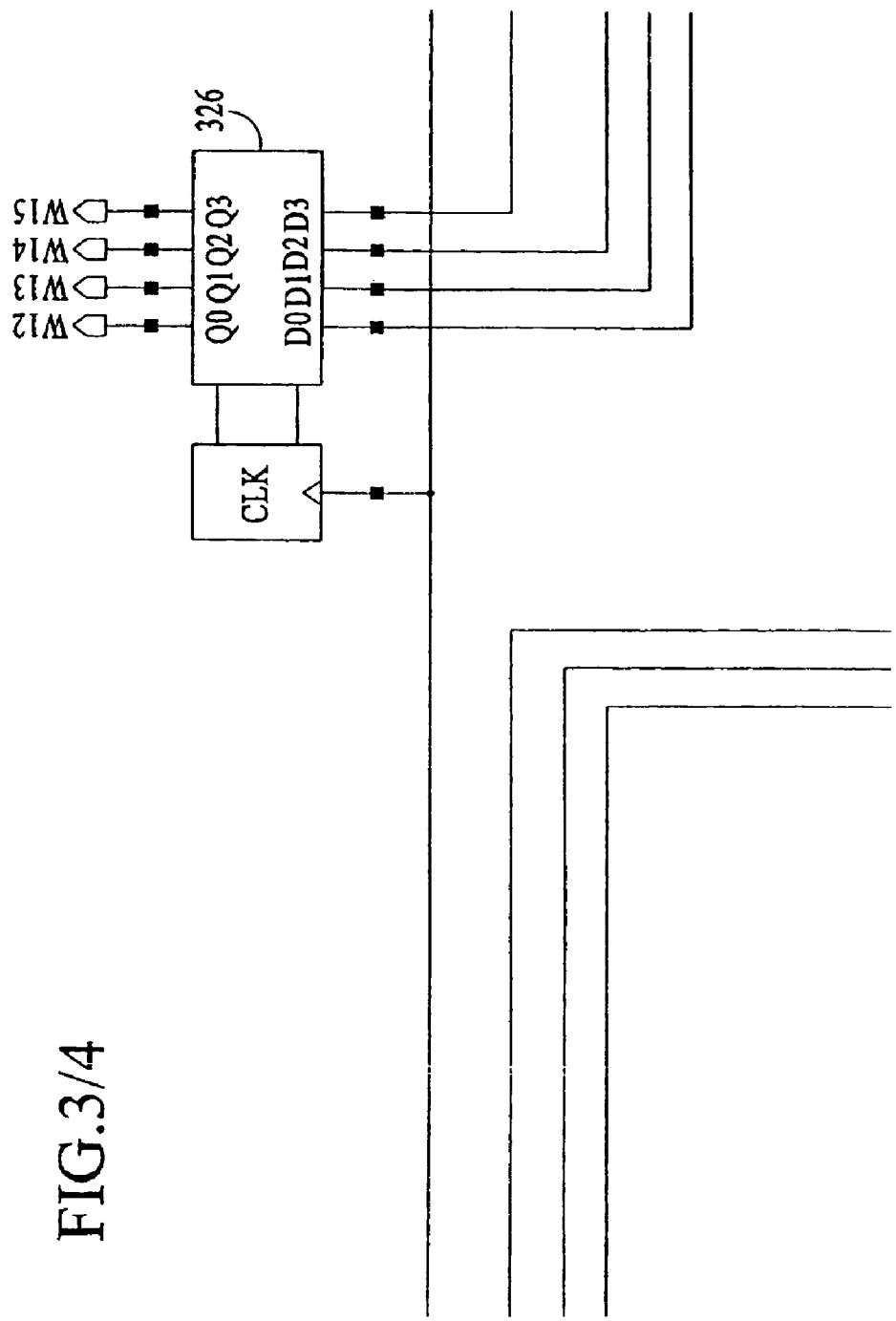
FIG.3/4

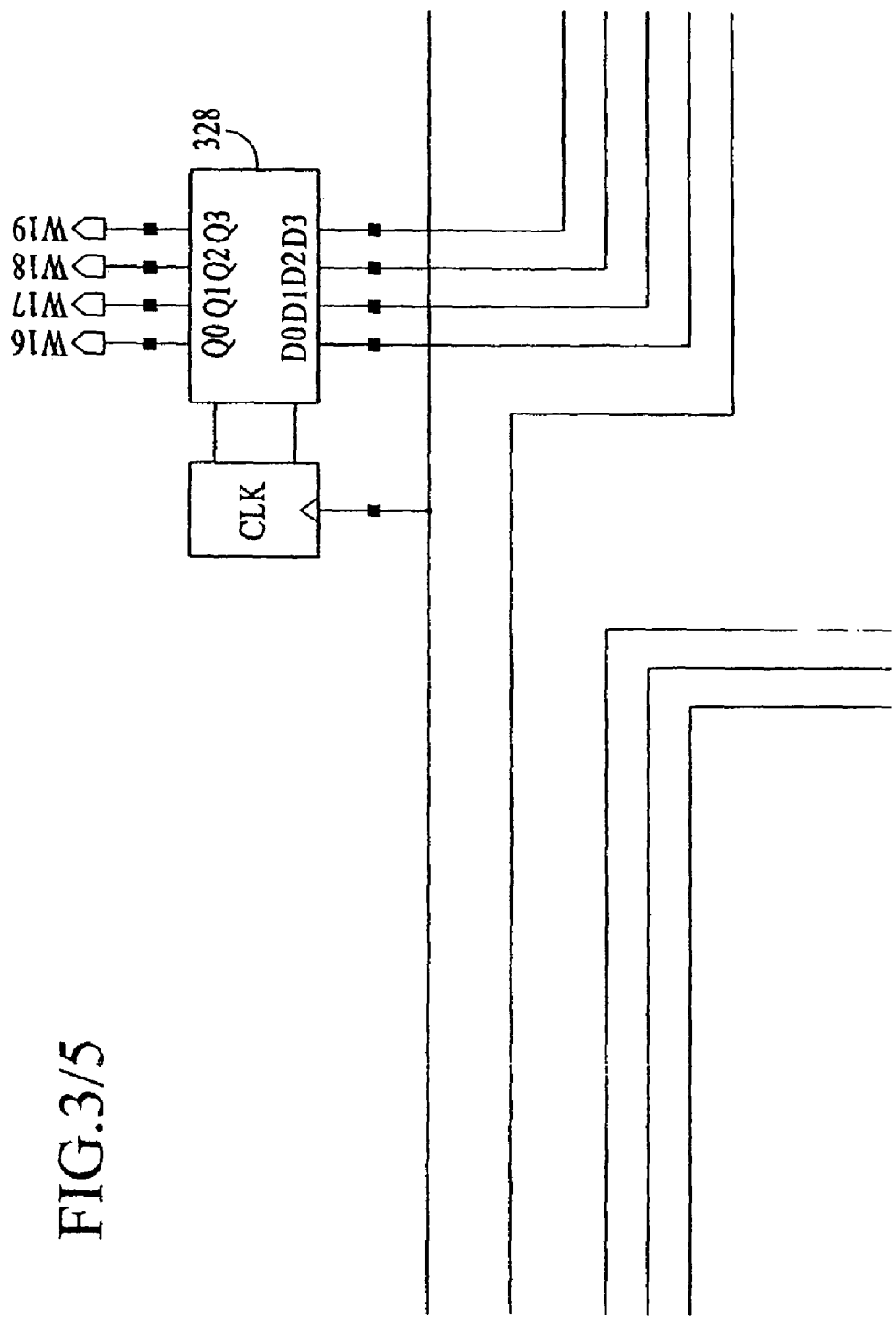
FIG.3/5

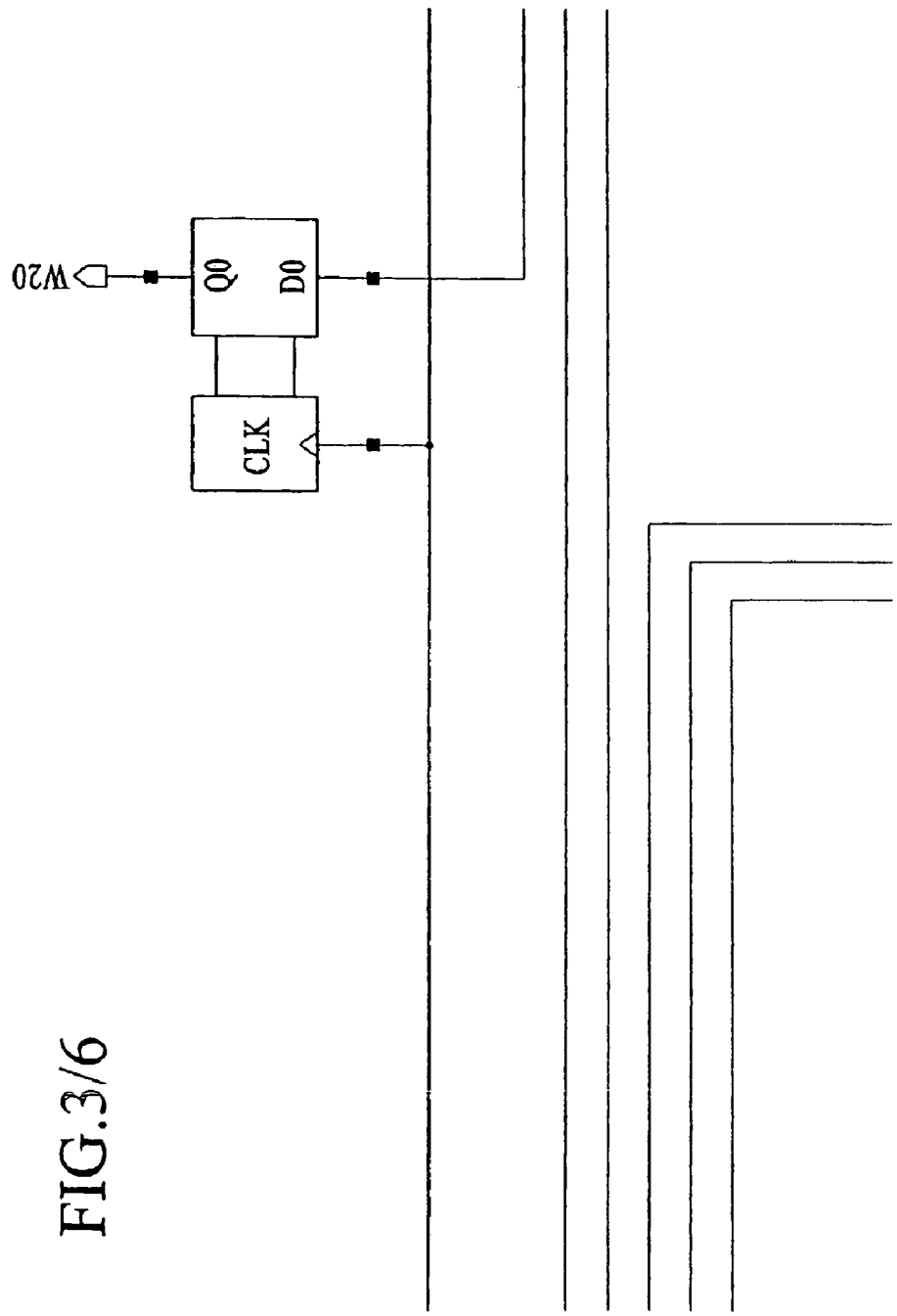
FIG.3/6

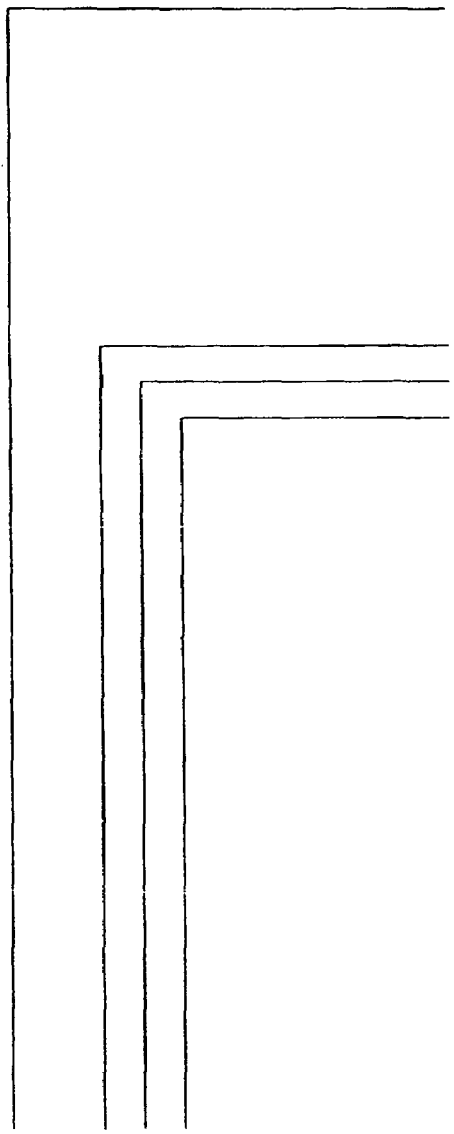
FIG.3/7

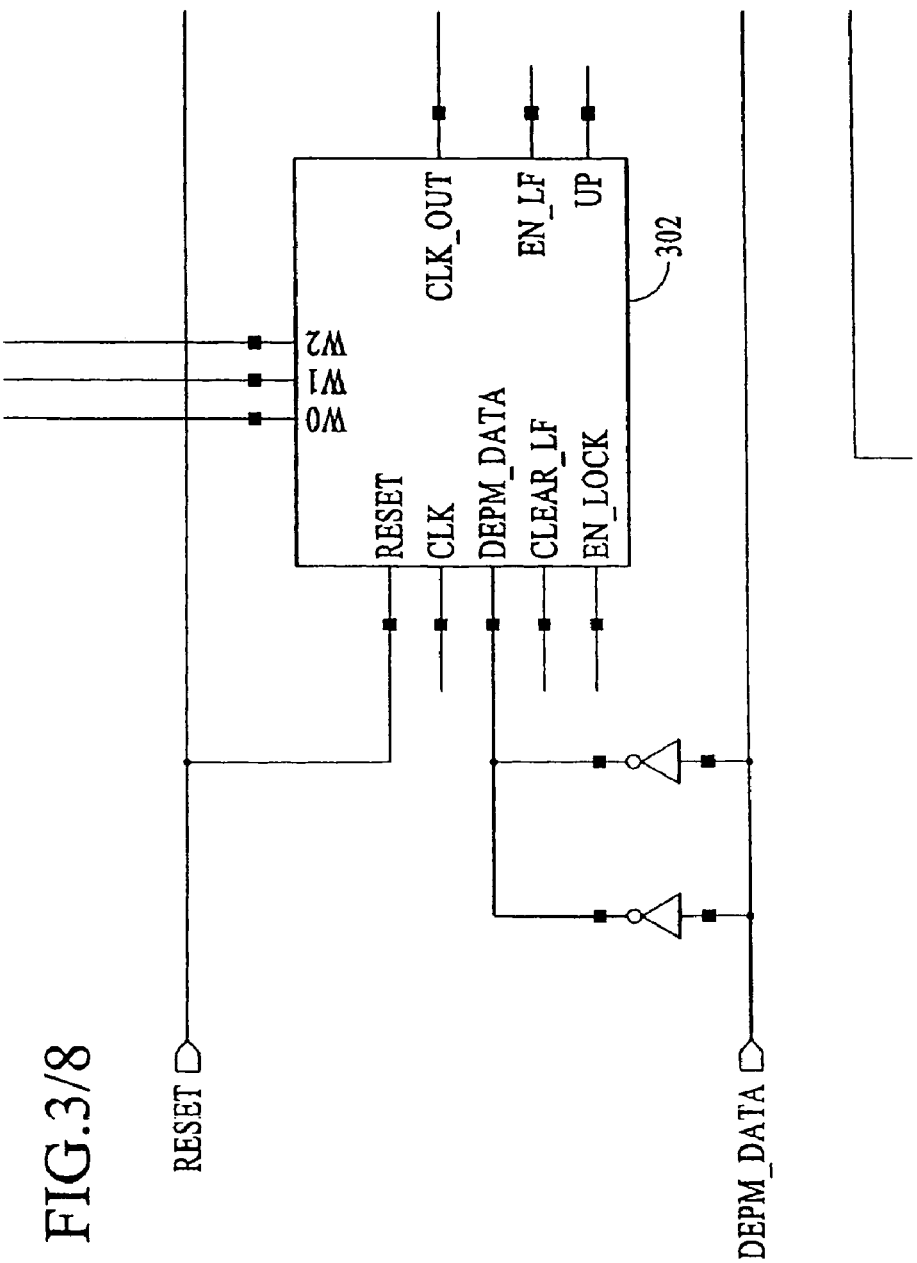
FIG.3/8

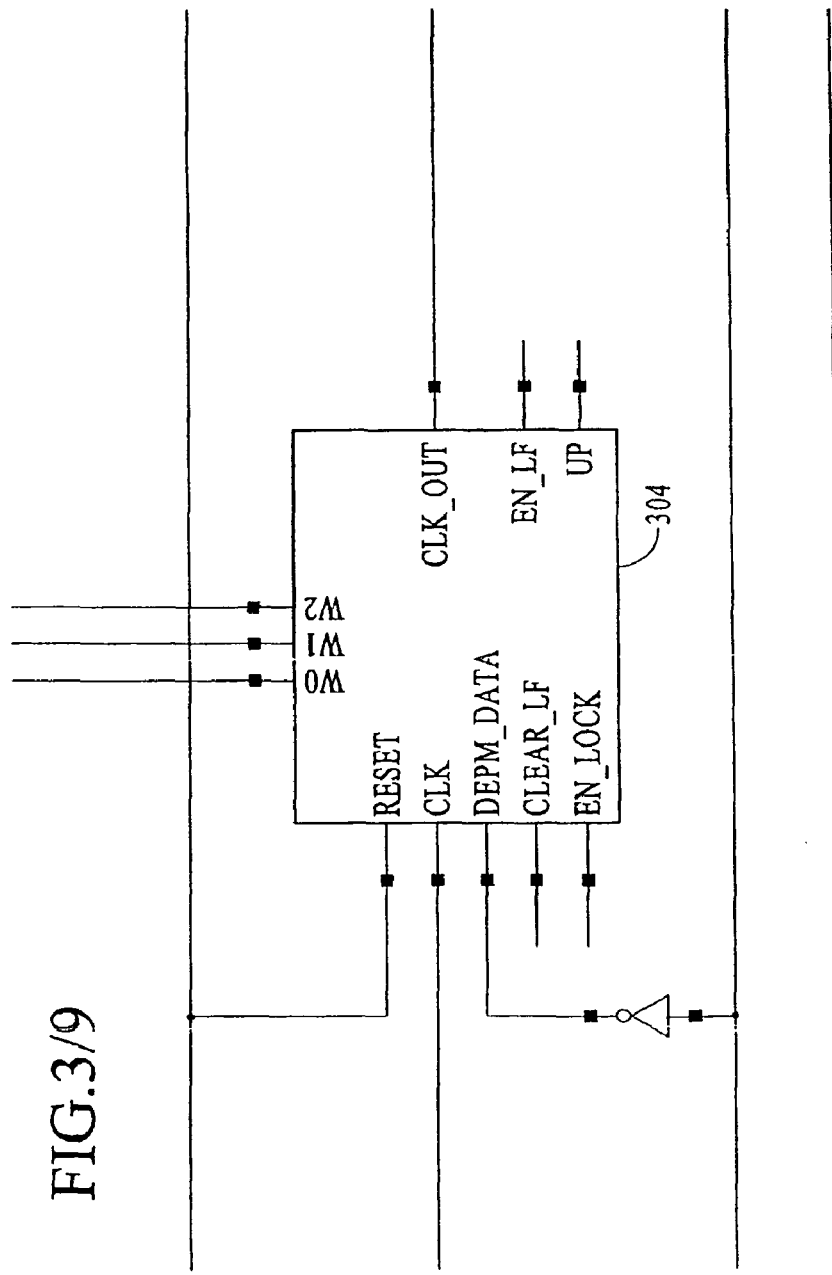
FIG.3/9

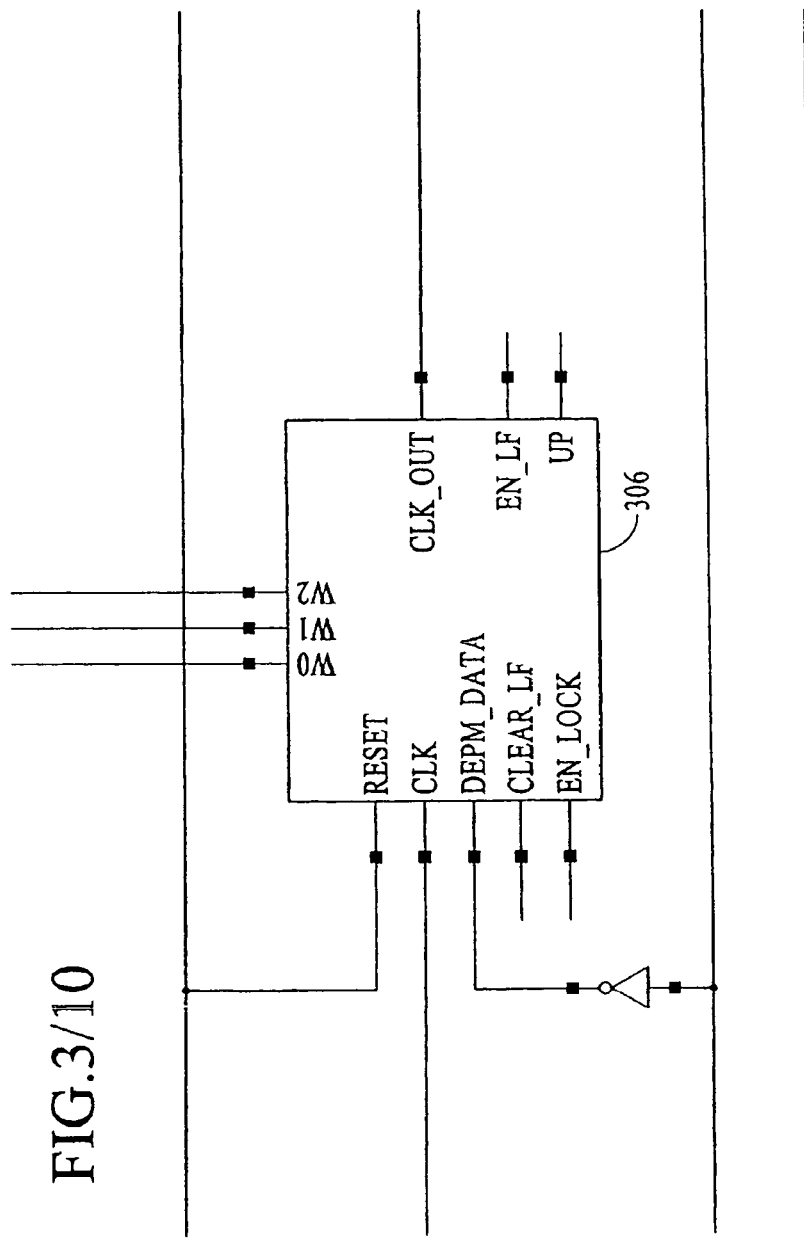
FIG.3/10

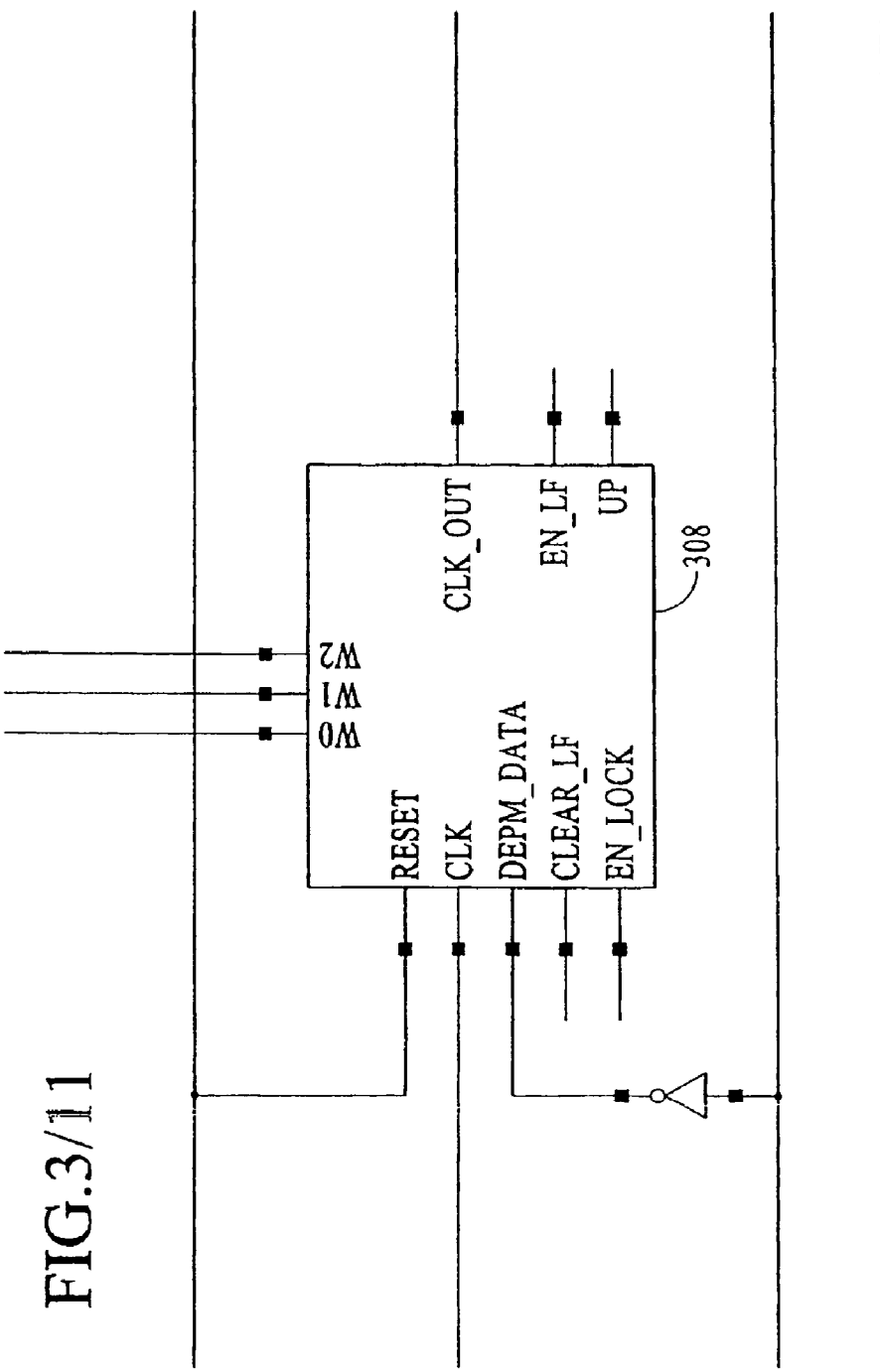
FIG.3/11

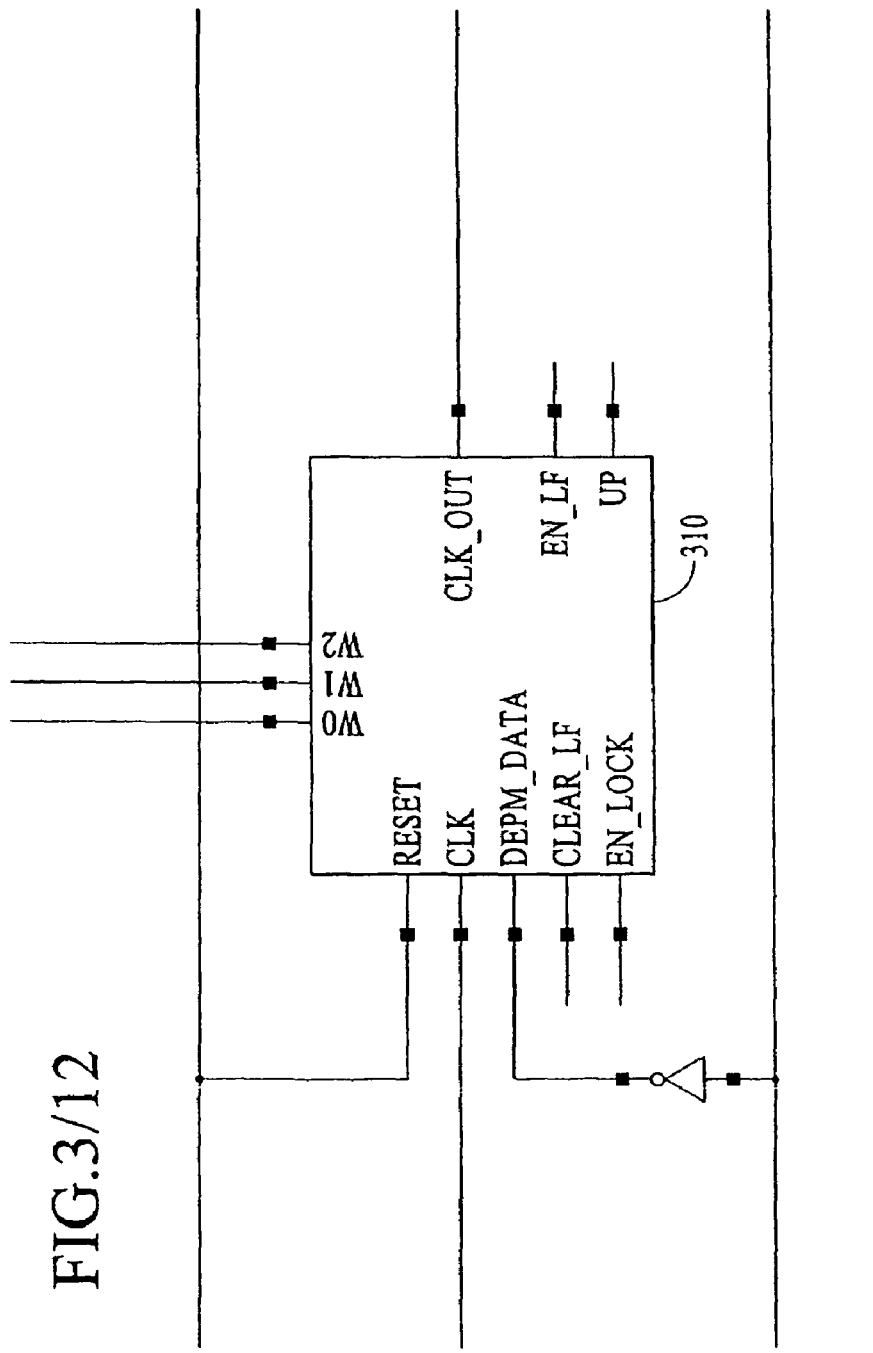
FIG.3/12

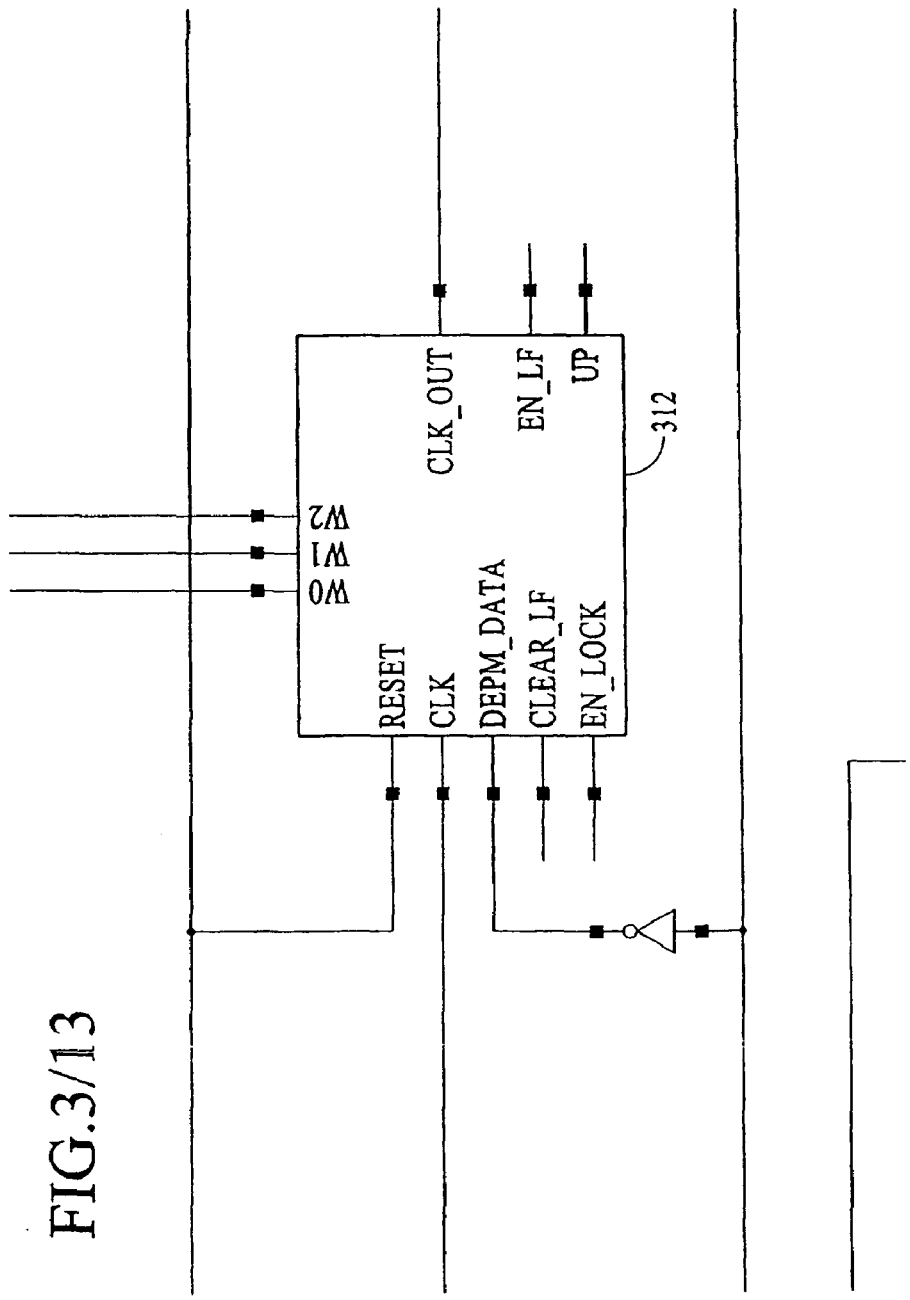
FIG.3/13

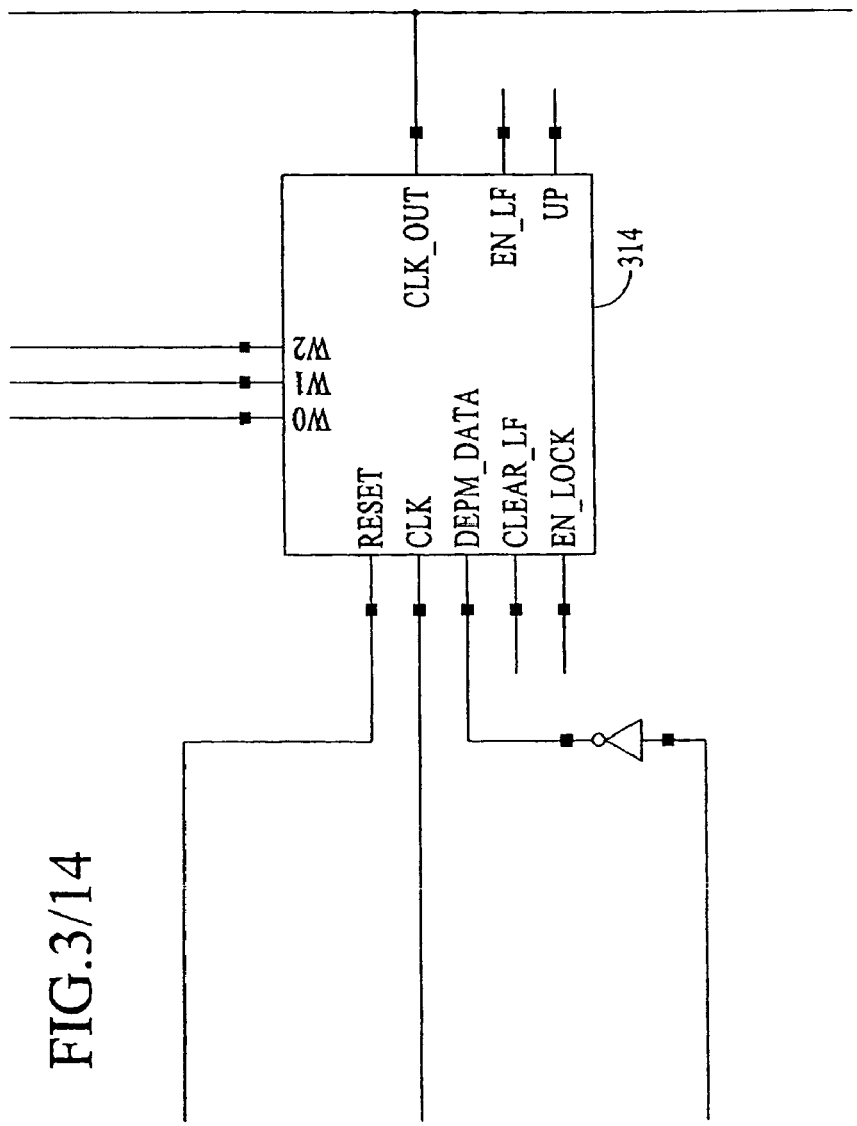
FIG.3/14

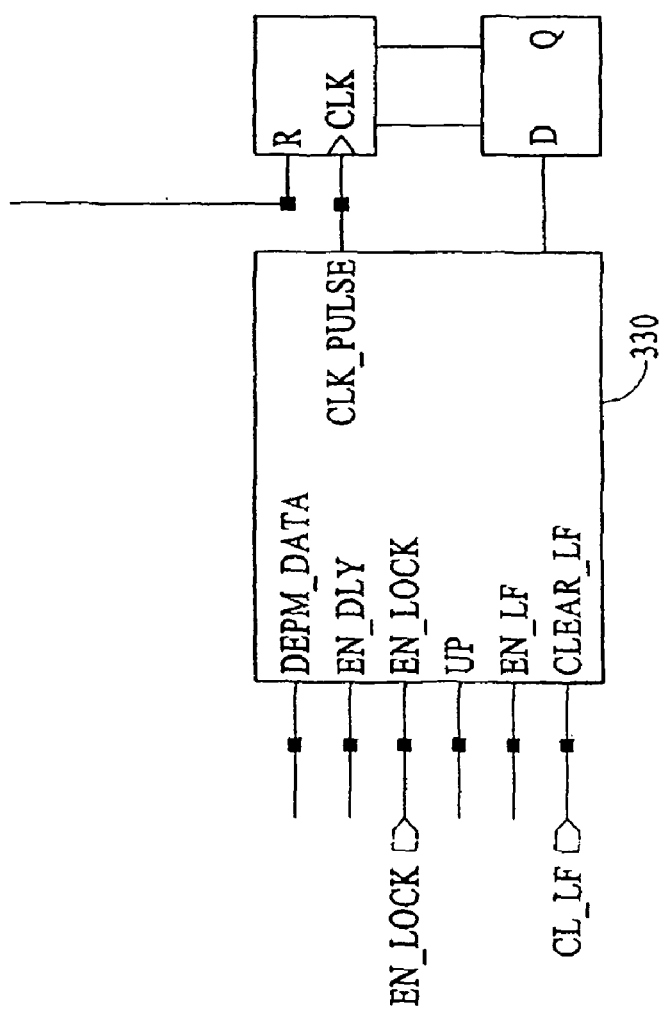
FIG.3/15

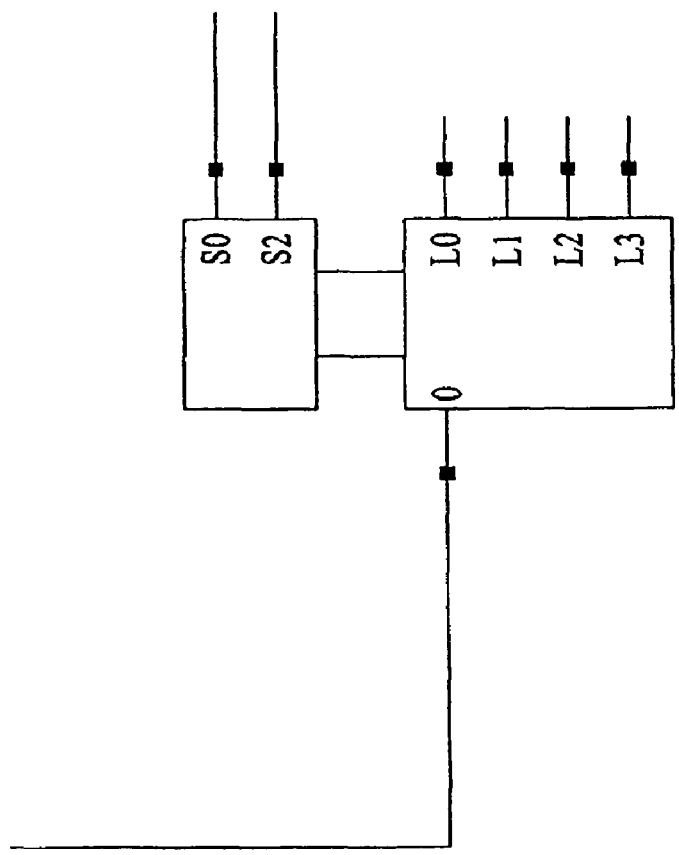
FIG.3/16

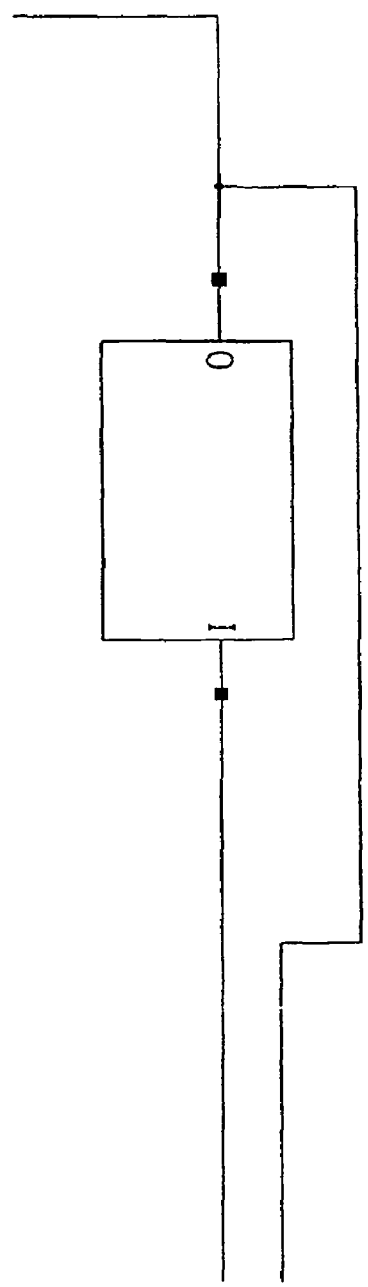
FIG.3/17

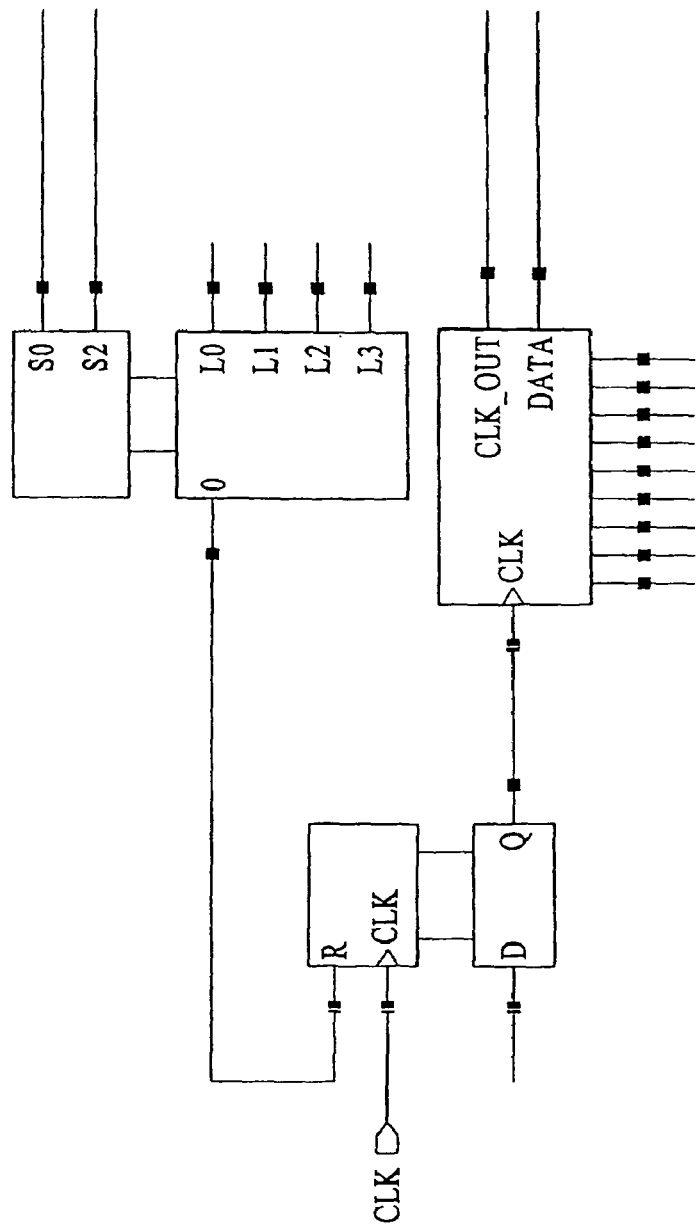
FIG.4/1

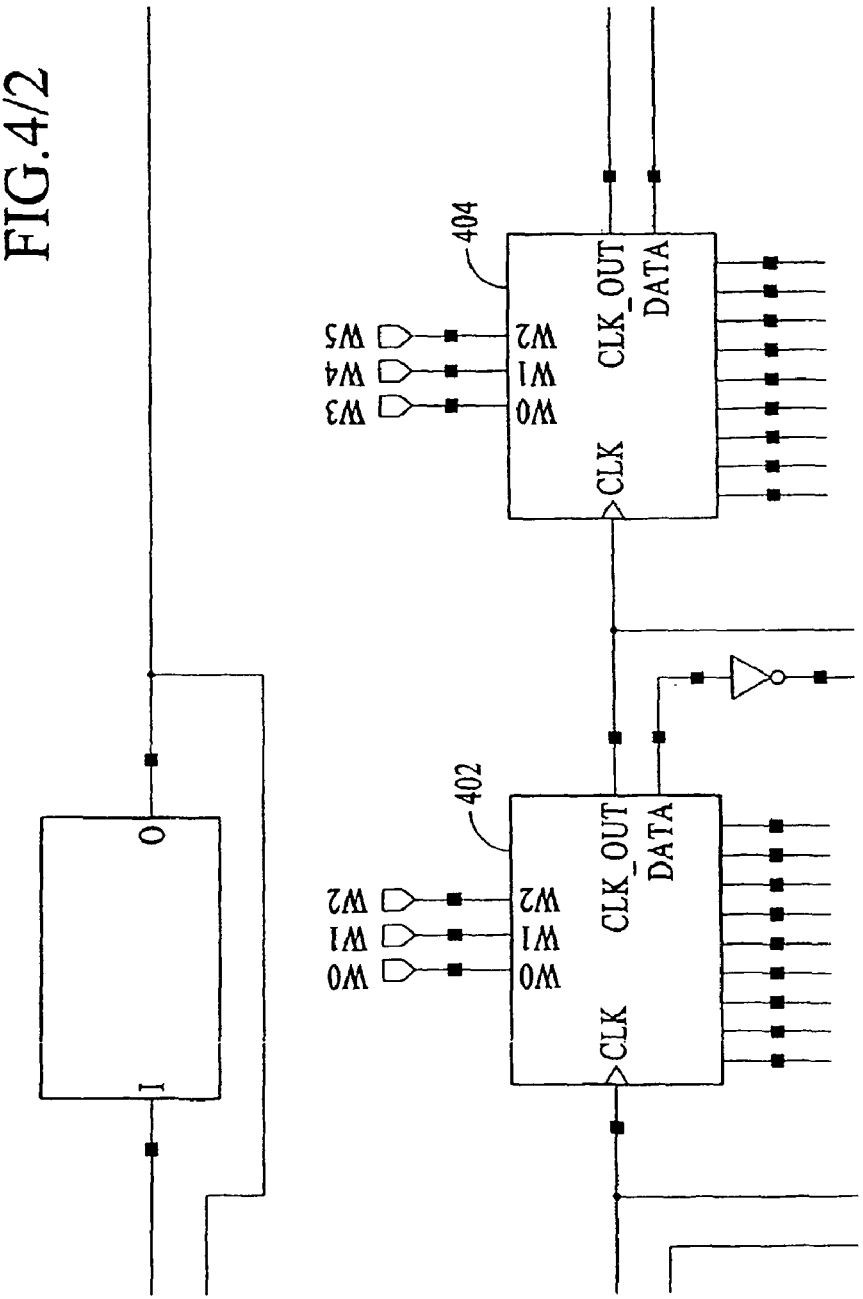
FIG.4/2

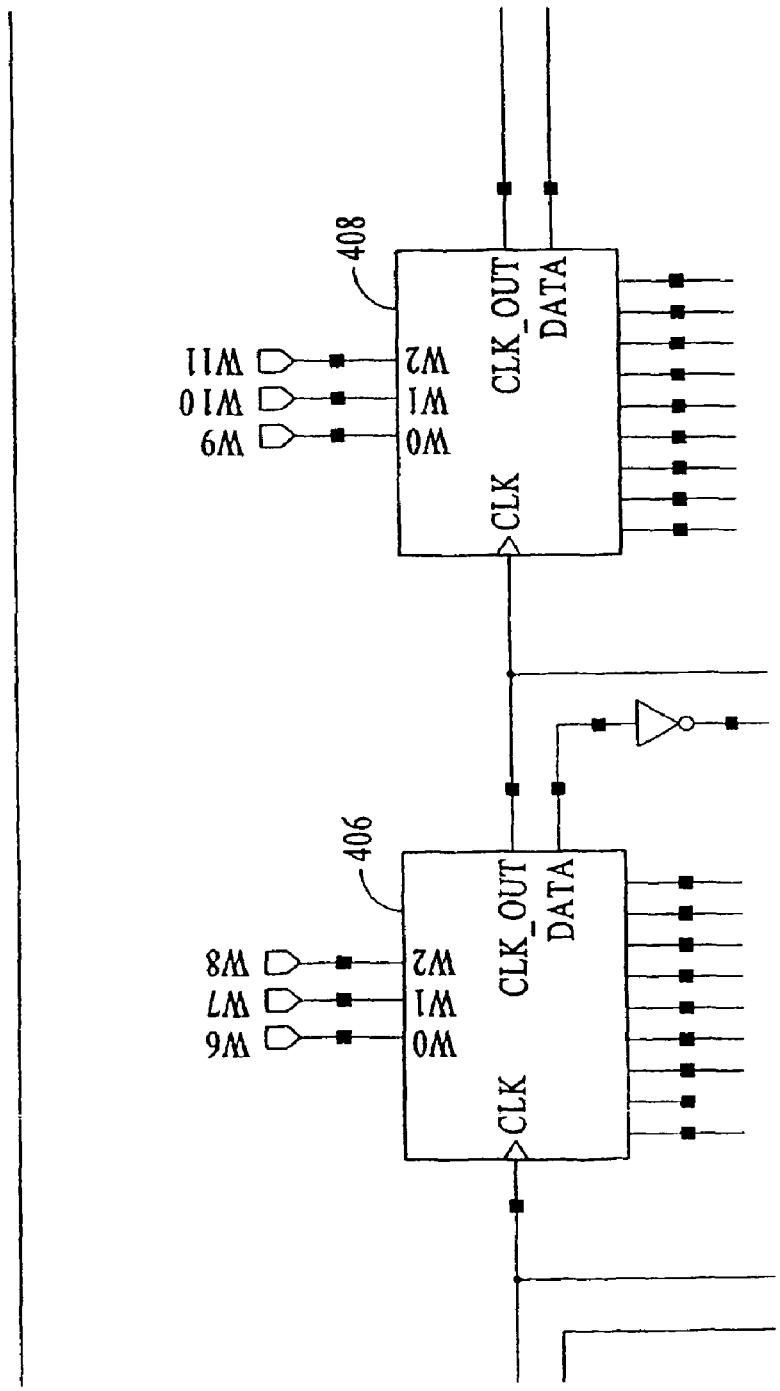
FIG.4/3

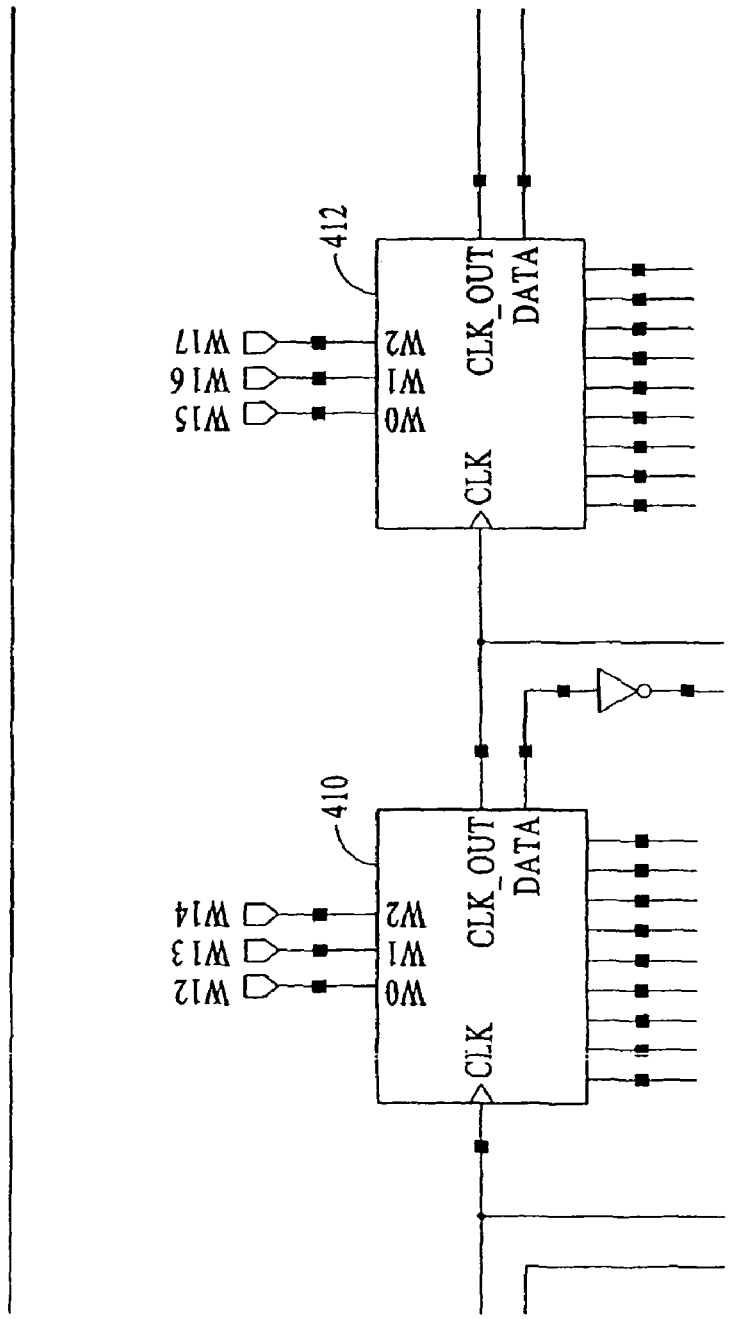
FIG.4/4

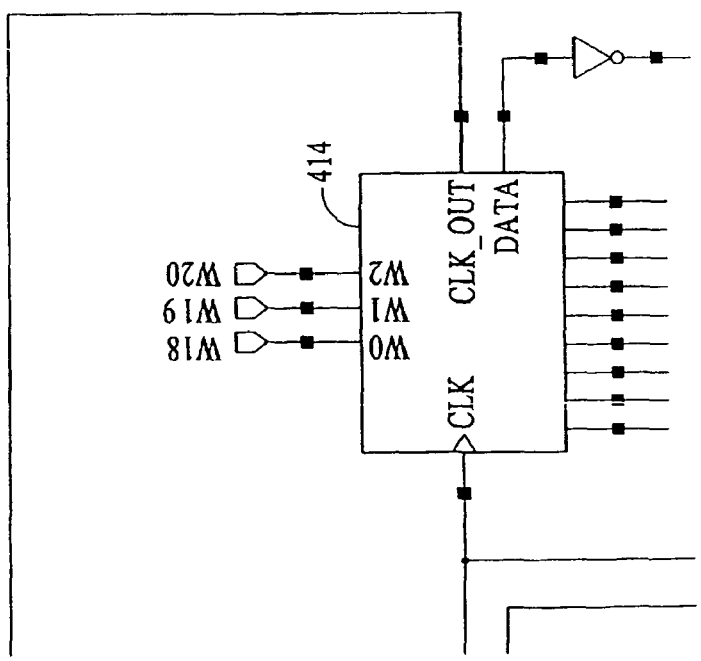
FIG. 4/5

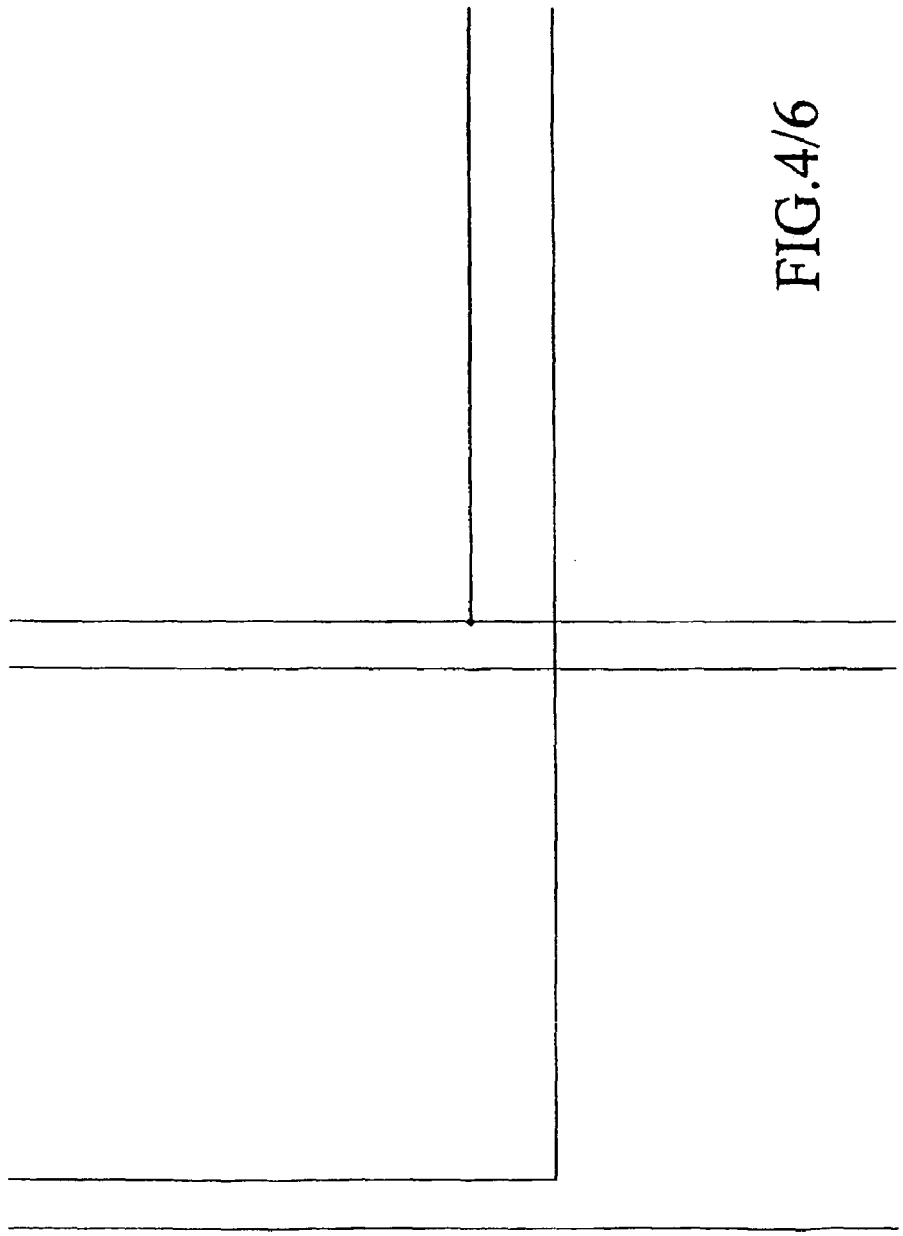
FIG.4/6

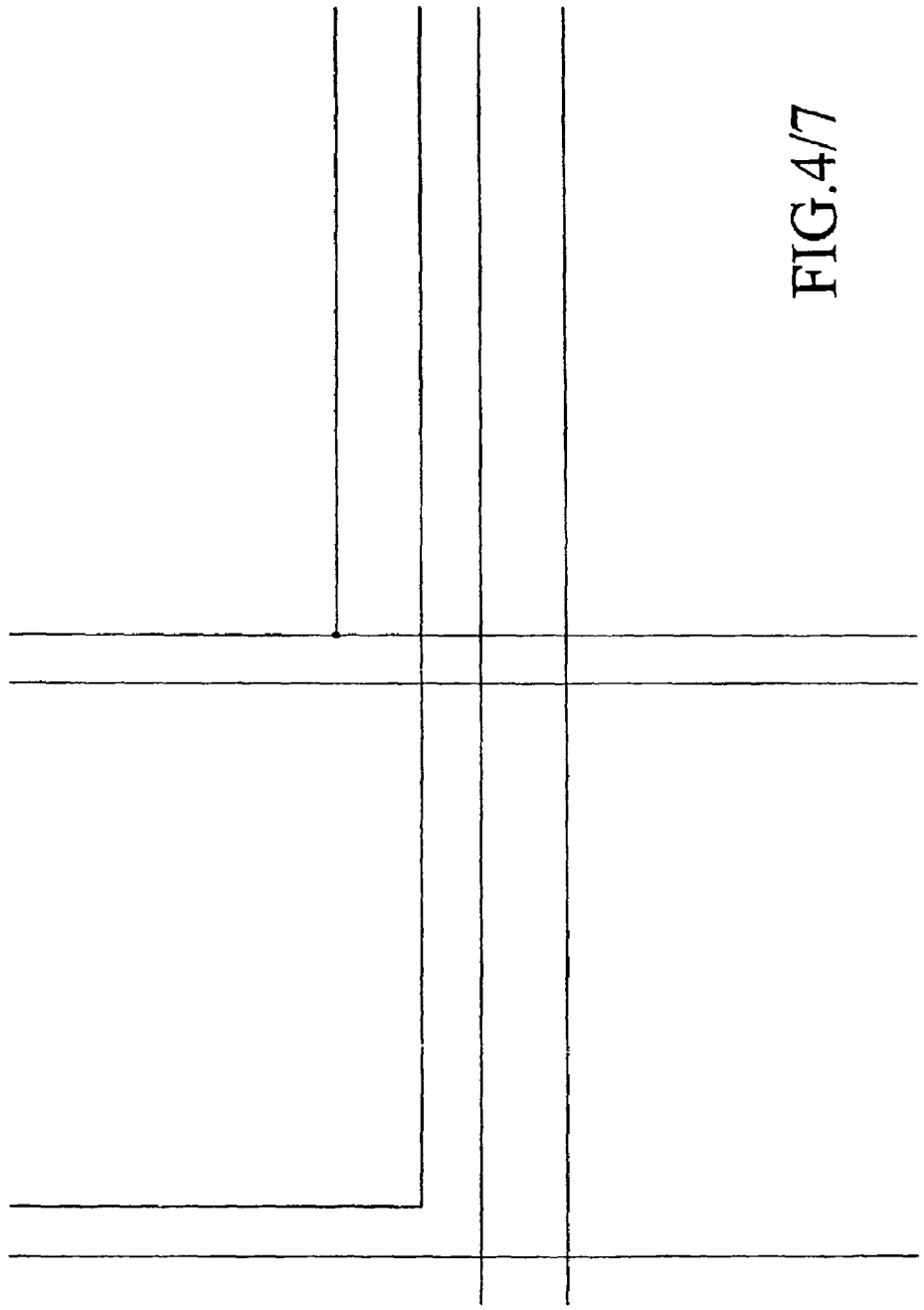
FIG.4/7

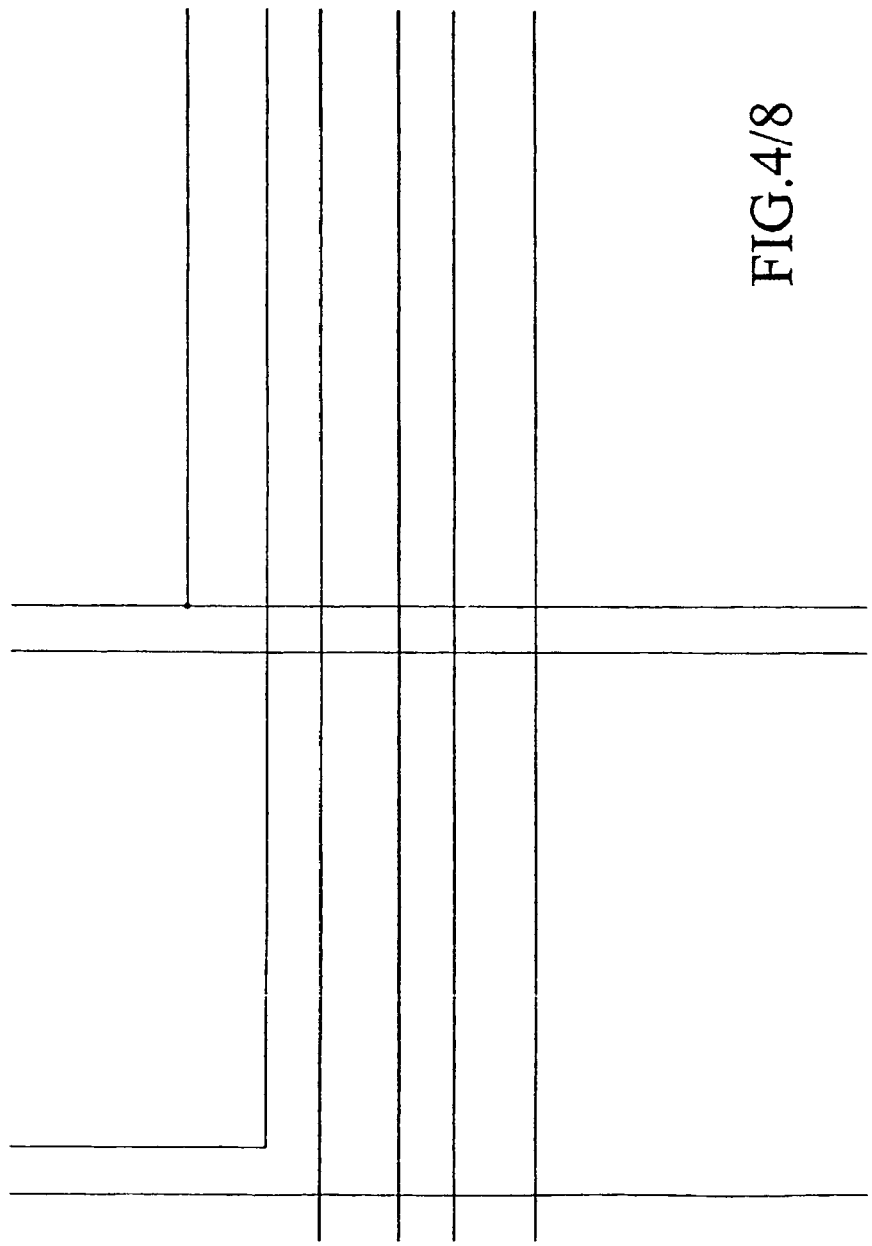
FIG. 4/8

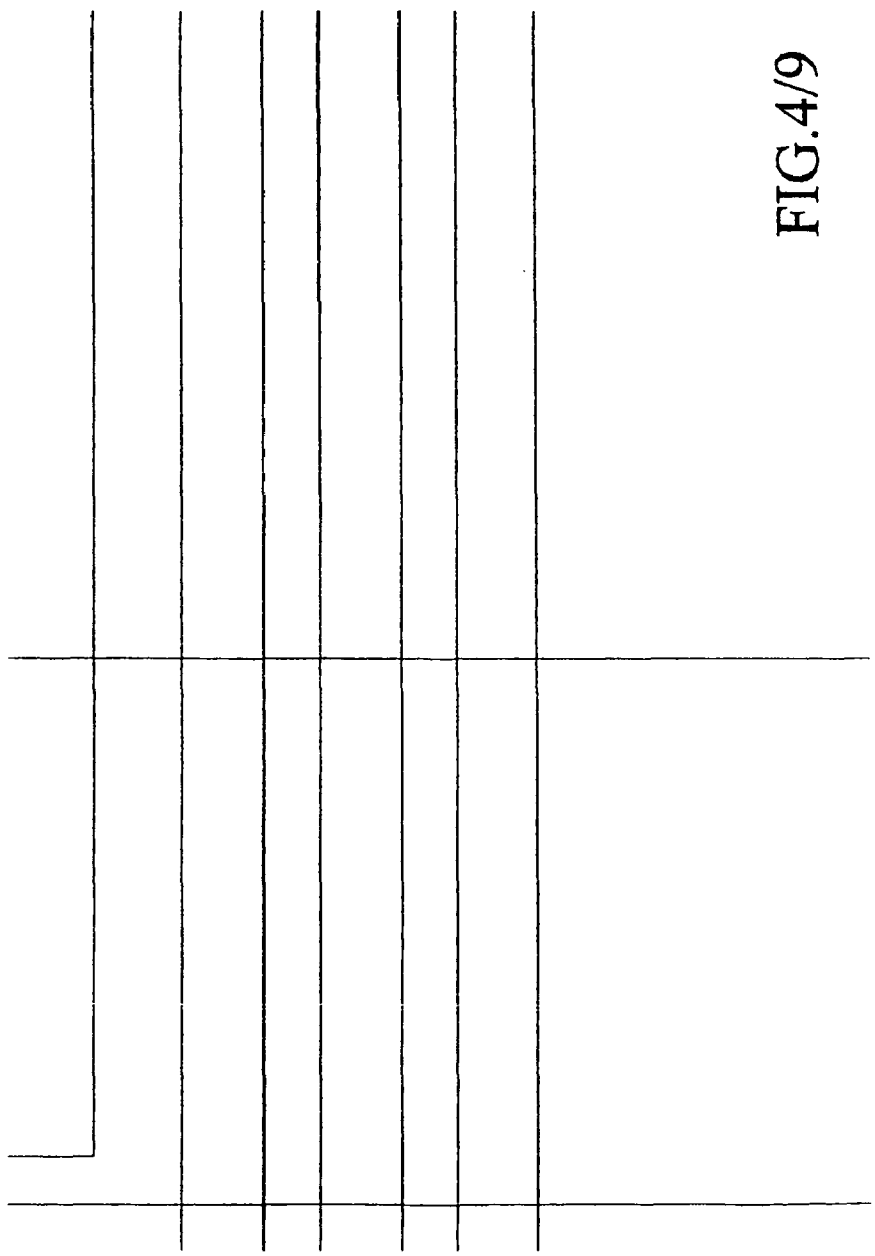
FIG.4/9

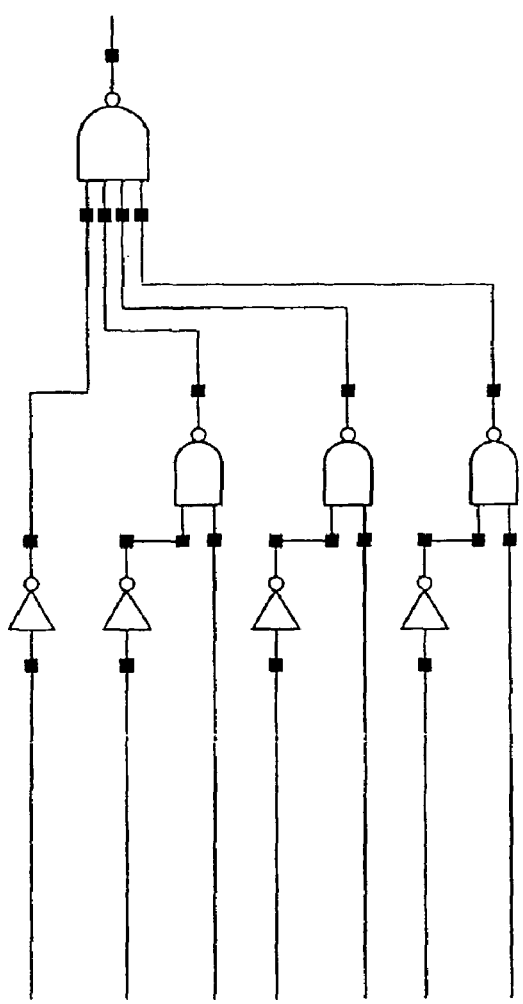
FIG.4/10

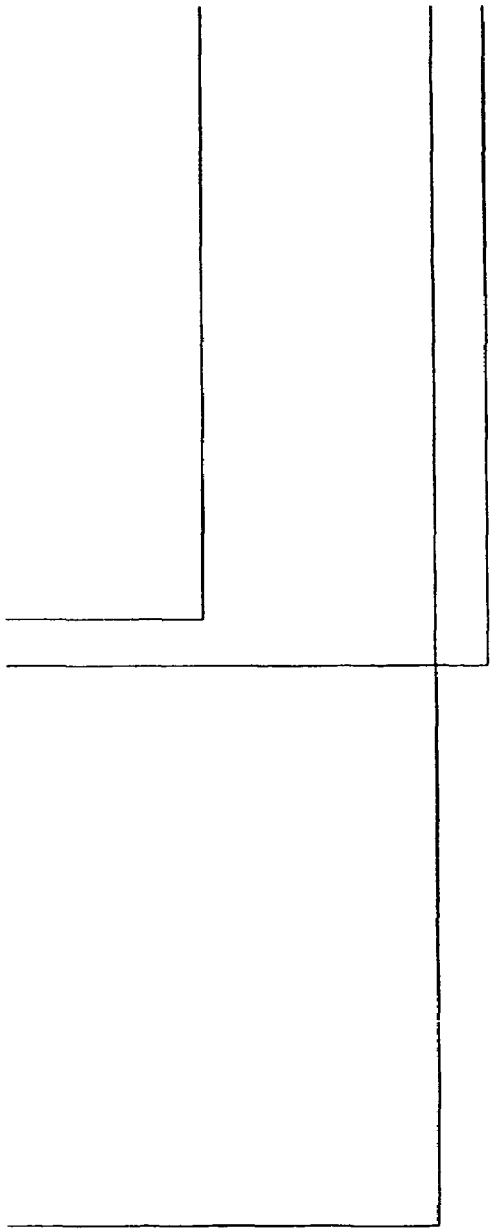
FIG.4/11

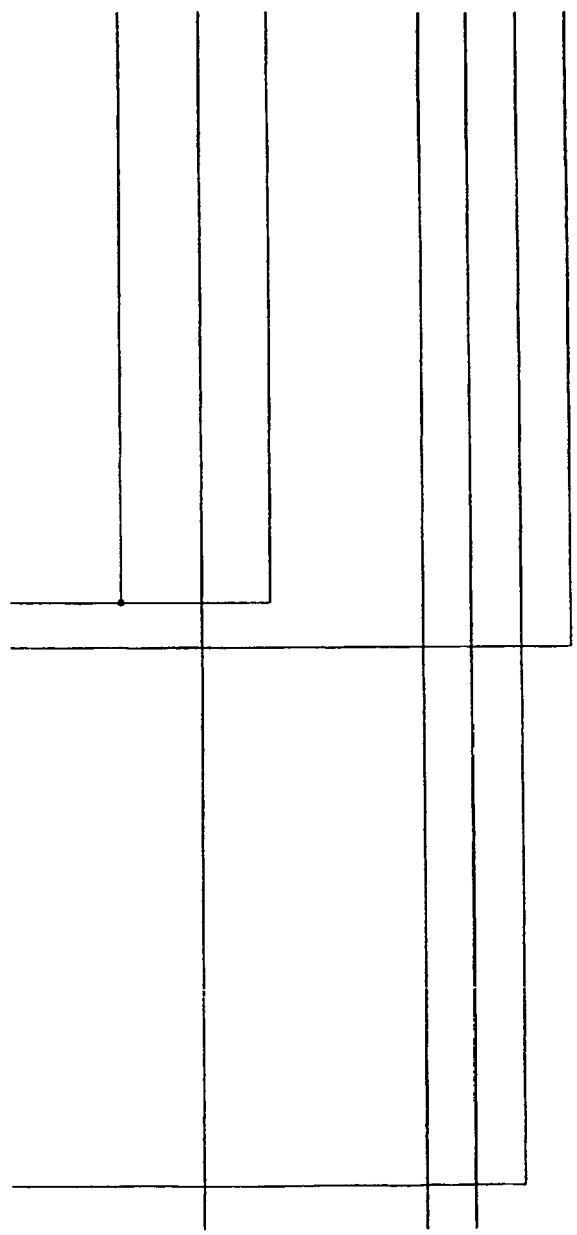
FIG.4/12

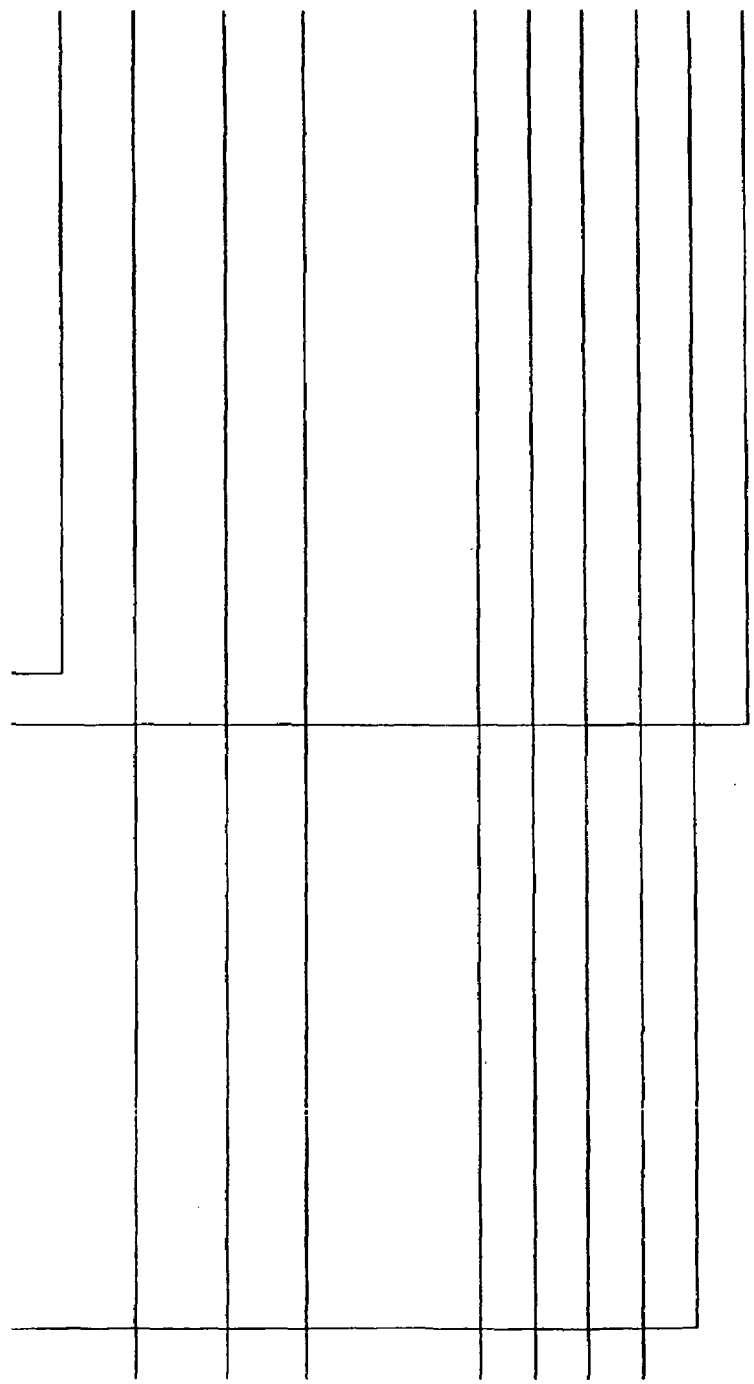
FIG.4/13

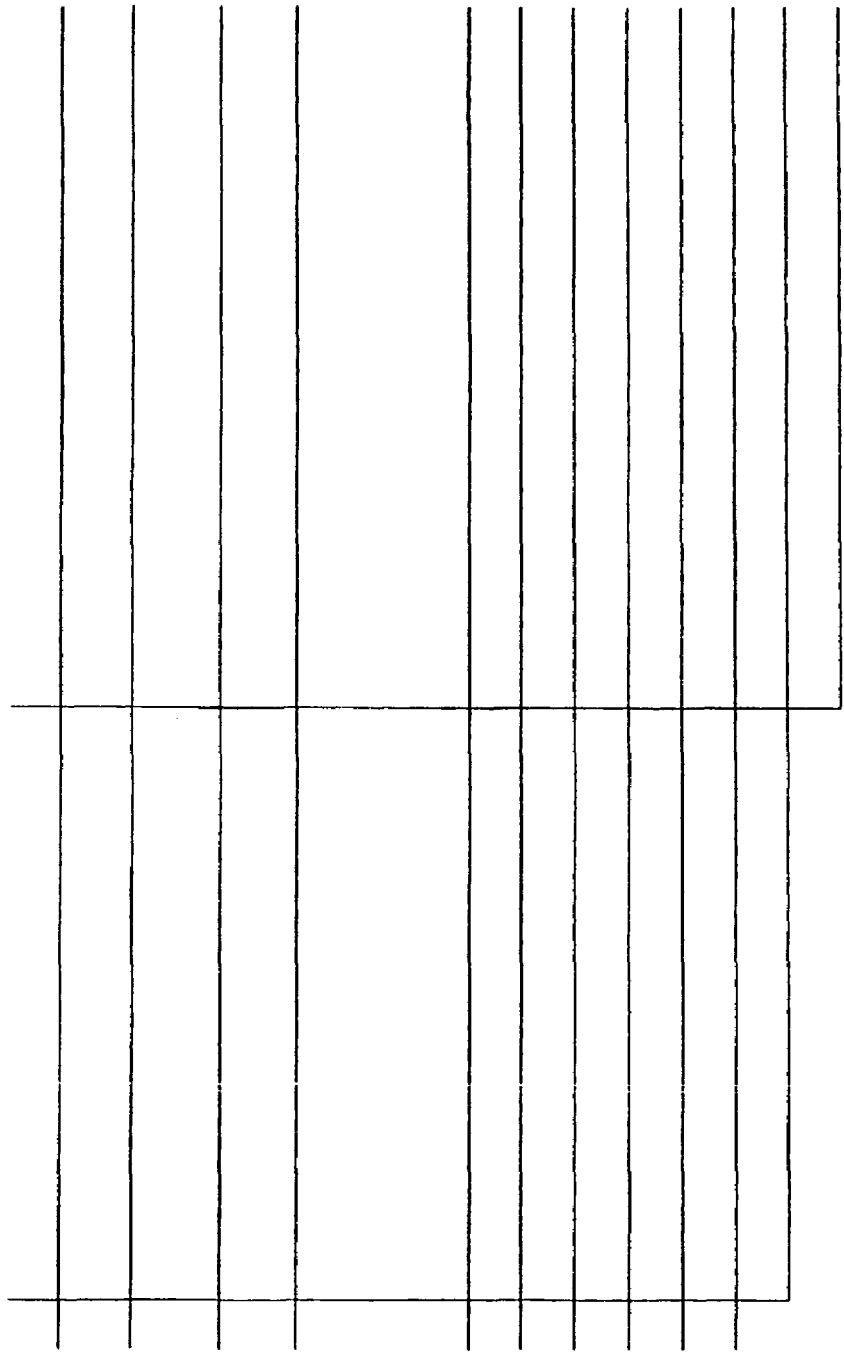
FIG.4/14

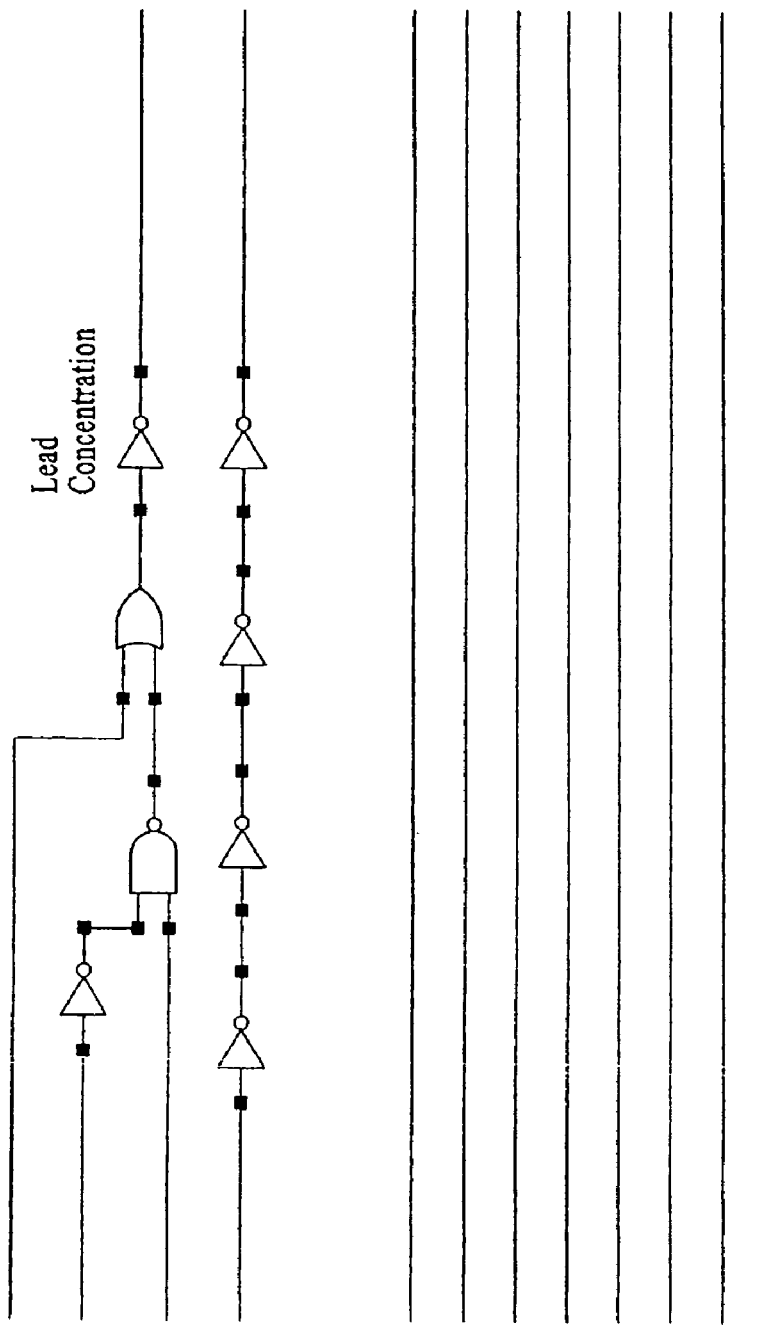
FIG.4/15

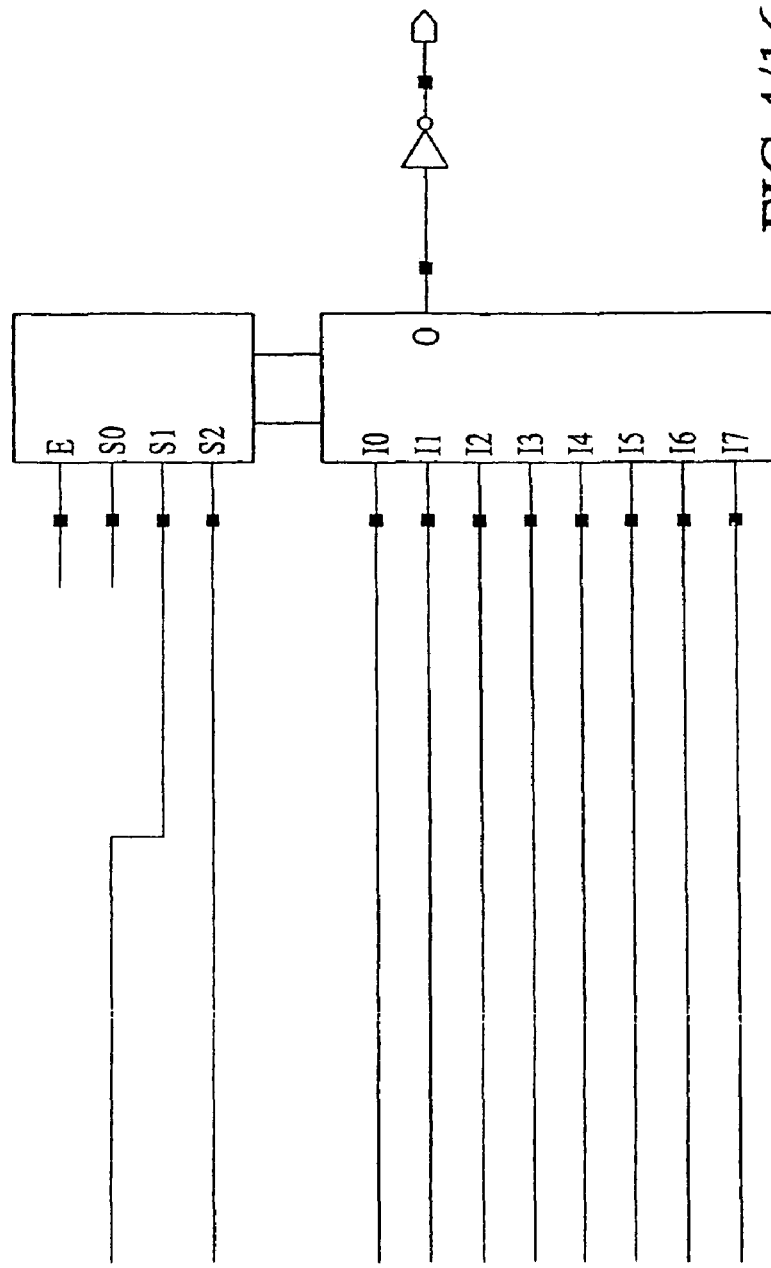
FIG.4/16

SYSTEM AND METHOD FOR CONTROLLING MODULATION

RELATED APPLICATIONS

This application is a continuation of U.S. patent application Ser. No. 10/972,990, filed on Oct. 25, 2004 now U.S. Pat. No. 7,440,515, the specification of which is incorporated herein by reference in its entirety.

FIELD OF THE INVENTION

The present invention relates to data transmission, and more particularly to a system and method for controlling modulation.

BACKGROUND OF THE INVENTION

High-speed serial data transmission between integrated circuits is a major source of power consumption due to high switching rates and driving currents associated with signal and clock transmission. One conventional solution is to use single-channel serial transmission (SCST), which causes a dynamic power draw. However, SCST suffers from board noise sensitivity. Another conventional solution is to use differential transmission, which is more immune to board noise. However, differential transmission requires twice as many board traces, making it expensive to manufacture. Also, differential transmission draws a significant amount of static current during operation.

Another conventional solution is to use frequency modulation techniques, which are effective at compressing data and providing noise immunity. However, these techniques require additional circuitry and do not address the high-power consumption issues. In fact, frequency modulation techniques consume too much power for most applications.

Accordingly, what is needed is an improved system and method for transmitting data. The system and method should be efficient, simple, cost effective and capable of being easily adapted to existing technology. The present invention addresses such a need.

SUMMARY OF THE INVENTION

A system and method for controlling modulation is disclosed. The system includes a plurality of modulators and a transmitting unit. The plurality of modulators decodes data from a data signal and also encodes the data into a clock signal. The transmitting unit transmits the encoded clock signal. According to the system and method disclosed herein, the present invention provides optimized coding efficiency while minimizing overall power consumption.

BRIEF DESCRIPTION OF THE DRAWINGS

FIG. 1 is a block diagram of a modulator in accordance with the present invention.

FIG. 1/1-1/16 illustrate portions of the bloack diagram of FIG. 1.

FIG. 3 is a block diagram showing phase modulators, which can be used to implement the phase modulators of FIG. 1, in accordance with the present invention.

FIG. 3/1-3/17 illustrate portions of the block diagram of FIG. 3.

FIG. 4 is a block diagram of a decoder, which can be used to implement one of the phase modulators of FIG. 3, in accordance with the present invention.

FIG. 4/1-4/16 illustrate portions of the block diagram of FIG. 4.

DETAILED DESCRIPTION OF THE INVENTION

Figure 2:
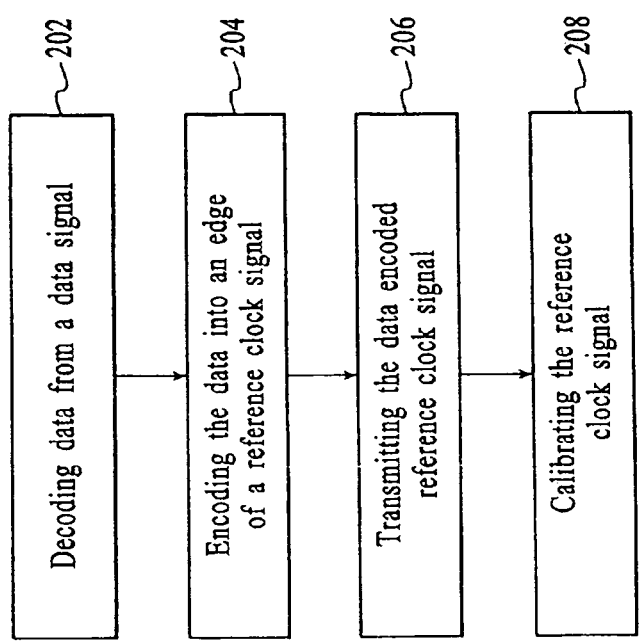
FIG. 2 is a flow chart showing a method for controlling phase modulation in accordance with the present invention.

The present invention relates to data transmission, and more particularly to a system and method for controlling phase modulation. The following description is presented to enable one of ordinary skill in the art to make and use the invention, and is provided in the context of a patent application and its requirements. Various modifications to the preferred embodiment and the generic principles and features described herein will be readily apparent to those skilled in the art. Thus, the present invention is not intended to be limited to the embodiment shown, but is to be accorded the widest scope consistent with the principles and features described herein.

A system and method in accordance with the present invention for controlling modulation are disclosed. The system includes a modulator that encodes data into a clock signal, where the encoding is based on relative phase positions. This optimizes coding efficiency and minimizes switching, which minimizes power consumption. To more particularly describe the features of the present invention, refer now to the following description in conjunction with the accompanying figures.

Although the present invention disclosed herein is described in the context of phase modulation and chip/board level signal transmission, the present invention may apply to other types of modulation and other levels of signal transmission and still remain within the spirit and scope of the present invention.

FIG. 1 is a block diagram of a modulator 100 in accordance with the present invention. In a specific embodiment, the modulator 100 is a 21-bit modulator, which includes phase modulators 102, 104, 106, 108, 110, 112, and 114. The phase modulators 102-114 are 3-bit phase modulators. The modulator 100 also includes 8-bit units 120, 122, 124, 126, 128, 130, 132, and 136, and feedback glitch filters 140 and 142.

FIG. 2 is a flow chart showing a method for controlling phase modulation in accordance with the present invention. Referring to both FIGS. 1 and 2 together, the modulator 100 decodes data from a data signal, in a step 202. Next, each of the phase modulators 102-114 encodes the data into an edge of a reference clock signal, in a step 204. Since the phase modulators 102-114 are 3-bit phase modulators, 3-bit words are encoded. Encoding 3 bits into each edge of the reference clock signal maximizes the amount of data in each transmission signal. While the phase modulators 102-114 are 3-bit phase modulators, the exact number of bits per modulator will depend on the specific application. Modulators of greater than 3-bits can be used is still remain within the spirit and scope of the present invention.

In this specific embodiment, there are seven 3-bit phase modulators 102-114. As a result, a total 21 bits of data are transmitted during each reference clock cycle. The exact number of 3-bit phase modulators will depend on the specific application. Next, the 8-bit units 120-136 transmit the data encoded reference clock signal, in a step 206.

Because data and clock information is combined into one transmission signal, the transmission signal can be transmitted at lower in frequency without compromising performance. Operating at lower frequencies contributes to lower overall power consumption. For example, by using a 3-bit encoding scheme in specific embodiments of the present invention, the signal switching rate can be reduced by 20% with respect to conventional serial transmission schemes. Furthermore, the phase modulators of the present invention consume little power by themselves and can be completely powered down while retaining settings in digital registers.

Furthermore, by minimizing the number of transmitting channels, the number of board traces is lowered. This makes the modulator 100 less susceptible to board noise. In addition, modulator 100 maintains a fixed switching rate, which makes it easier to transmit and recover data.

Next, the feedback filters 140 and 142 calibrate a reference clock signal, in a step 208. This prevents glitches along the transmission line. The calibrating is accomplished by resetting the reference clock after the data has been transmitted through the modulator 100. This self-reset feature is done automatically and provides calibration with respect to the specific data set that is transmitted in a particular edge. Automatically resetting the reference clock eliminates phase error accumulation and compensates for process variation. This also ensures that each edge is later decoded correctly.

FIG. 3 is a block diagram showing phase modulators 302, 304, 306, 308, 310, 312, and 314, which can be used to implement the phase modulators 102-114 of FIG. 1, respectively, in accordance with the present invention. Storage registers 320, 322, 324, 326, and 328 store data provided by the phase modulators 302-314. The storage registers 320-328 together store 21 bits of data, which are subsequently transmitted in the reference clock signal.

In operation, generally, the phase modulators 302-314 decode data from a data signal, which is received via an input unit 330. The input unit 330 reads in the first edge of a data signal and then feeds the first edge into each of the phase modulators 302-314. In a specific embodiment, the first edge is a rising edge. Each of the phase modulators 302-314 enables an edge of the transmission signal to carry a 3-bit digital value. The seven 3-bit modulators output a total of 21 bits of data. The storage registers 230-238 store the 21 bits.

Figure 4:
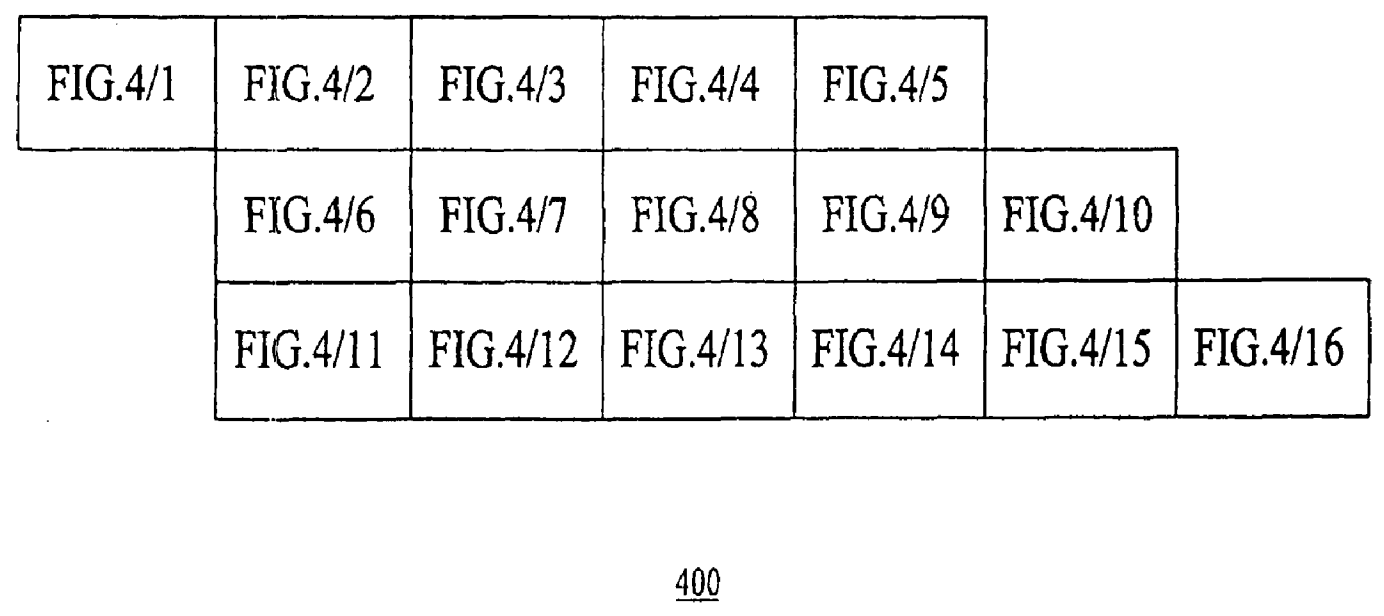

FIG. 4 is a block diagram of a decoder 400, which can be used to implement one of the phase modulators 302-314 of FIG. 3, in accordance with the present invention. The decoder 400 is a 3-bit decoder and includes filters 402, 404, 406, 408, 410, 412, and 414. In a specific embodiment, the filters 402-414 are 8-bit finite impulse response (FIR) counter filters. Each of the filters 402-414 stores an 8-bit value, providing high performance on a granular scale.

In operation, the decoder 400 decodes data from a data signal. Each filter 402-414 then reads a phase position from a delay chain. Based on the decoded data and the phase readings, the decoder 400 outputs a 3-bit digital value that indicates one of eight possible phase positions. The 3-bit digital value represents a 3-bit word, which is subsequently combined with other 3-bit words from other decoders to provide a 21-bit word.

The phase positions are relative to a reference phase provided by the reference clock. The decoder 400 is asynchronous in that the reference clock is separate and independent from the system clock. Accordingly, the decoder 400 does not rely on the system clock to decode or to generate the phase reference. This is possible because the modulator 100 is data-locked to a reference clock signal.

According to the system and method disclosed herein, the present invention provides numerous benefits. For example, data-locked dual-edge phase modulation (DEPM) is provided with optimized coding efficiency and minimized power consumption. Embodiments of the present invention also provide a fixed switching rate and high noise rejection, eliminate phase error accumulation, and compensate for process variation.

A system and method for controlling modulation has been disclosed. The system includes a modulator that encodes data into a clock signal. This optimizes coding efficiency and minimizes switching, which minimizes power consumption.

The present invention has been described in accordance with the embodiments shown. One of ordinary skill in the art will readily recognize that there could be variations to the embodiments, and that any variations would be within the spirit and scope of the present invention. For example, the present invention can be implemented using hardware, software, a computer readable medium containing program instructions, or a combination thereof. Software written according to the present invention is to be either stored in some form of computer-readable medium such as memory or CD-ROM, or is to be transmitted over a network, and is to be executed by a processor. Consequently, a computer-readable medium is intended to include a computer readable signal, which may be, for example, transmitted over a network. Accordingly, many modifications may be made by one of ordinary skill in the art without departing from the spirit and scope of the appended claims.

What is claimed is:

1. A modulator circuit comprising:
   a plurality of modulators that decode data from a data signal and encode the decoded data, based on relative phase positions, into a clock signal, wherein each of the plurality of modulators comprises a plurality of decoders, each decoder of the plurality of decoders decodes data from the data signal, reads a phase position from a delay chain, and outputs a value that indicates a phase position; and
   a feedback filter that is coupled to the plurality of modulators and automatically calibrates the encoded clock signal after the encoded clock sign is transmitted.

2. The circuit of claim 1, wherein the clock signal is reset after the encoded clock signal has been transmitted.

3. The circuit of claim 1, wherein the clock signal is reset automatically.

4. The circuit of claim 1, wherein each of the plurality of modulators is at least a 3-bit modulator.

5. The circuit of claim 1, wherein each of the plurality of modulators outputs a value that indicates a phase position.

6. The circuit of claim 5, wherein the value represents a word.

7. The circuit of claim 6, wherein the word is combined with other words from other decoders of the plurality of decoders to provide at least a 21-bit word.

8. The circuit of claim 7, wherein the plurality of modulators encodes the decoded data into an edge of the clock signal.

9. The circuit of claim 1, wherein the plurality of modulators encodes the decoded data into an edge of the clock signal.

10. A modulator circuit comprising:
    a plurality of modulators that decode data from a data signal and encode the decoded data, based on relative phase positions, into a clock signal, wherein the plurality of modulators encodes data into an edge of the clock signal; and
    a feedback filter that is coupled to the plurality of modulators and automatically calibrates the clock signal after the encoded clock signal is transmitted.

11. The circuit of claim 10, wherein the clock signal is reset after the encoded clock signal has been transmitted.

12. The circuit of claim 10, wherein the clock signal is reset automatically.

13. The circuit of claim 10, wherein each of the plurality of modulators is at least a 3-bit modulator.

14. The circuit of claim 10, wherein each of the plurality of modulators outputs a value that indicates a phase position.

15. The circuit of claim 14, wherein the value represents a word.

16. The circuit of claim 15, wherein the word is combined with other words from other decoders of the plurality of decoders to provide at least a 21-bit word.

* * * * *